(12) United States Patent
Cleary et al.

(10) Patent No.: US 9,150,559 B2
(45) Date of Patent: Oct. 6, 2015

(54) ANTI-PROLIFERATIVE COMPOUNDS AND METHODS FOR USING THE SAME

(75) Inventors: Michael L. Cleary, Eugene, OR (US); Christina Matheny, San Francisco, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 14/117,571

(22) PCT Filed: May 15, 2012

(86) PCT No.: PCT/US2012/037936
§ 371 (c)(1),
(2), (4) Date: Jul. 14, 2014

(87) PCT Pub. No.: WO2012/158691
PCT Pub. Date: Nov. 22, 2012

(65) Prior Publication Data
US 2014/0323524 A1    Oct. 30, 2014

Related U.S. Application Data

(60) Provisional application No. 61/488,103, filed on May 19, 2011.

(51) Int. Cl.
*A61K 31/44* (2006.01)
*C07D 413/12* (2006.01)
*C07D 263/32* (2006.01)

(52) U.S. Cl.
CPC ............ *C07D 413/12* (2013.01); *C07D 263/32* (2013.01)

(58) Field of Classification Search
None
See application file for complete search history.

(56) References Cited

U.S. PATENT DOCUMENTS

| 6,822,097 B1 | 11/2004 | Norman et al. |
| 2007/0213378 A1 | 9/2007 | Thomas et al. |
| 2010/0298301 A1 | 11/2010 | Reader et al. |
| 2012/0225862 A1 | 9/2012 | Sutphin et al. |

FOREIGN PATENT DOCUMENTS

| WO | WO 2012/051117 | 4/2012 |
| WO | WO 2012051117 A2 * | 4/2012 |
| WO | WO 2012100223 A1 * | 7/2012 |

OTHER PUBLICATIONS

Valk, Prognostically Useful Gene Expression Profiles in Acute Myeloid Leukemia, New England Journal of Medicine, 2004, vol. 350, pp. 1617-1628.
Okada, Yuki et al., hDOT1L Links Histone Methylation to Leukemogenesis, Cell, vol. 121, pp. 167-178, Apr. 22, 2005.
Krivtsov, Andrei V. et al., MLL translocation, histone modifications and leukaemia stem-cell development, 2007, vol. 7, Nature Reviews/Cancer, Nature Publishing Group.

* cited by examiner

*Primary Examiner* — Heidi Reese
(74) *Attorney, Agent, or Firm* — Bozicevic, Field & Francis LLP

(57) ABSTRACT

Disclosed herein are anti-proliferative compounds which find use in inhibiting the growth of cancer cells. Also provided herein are methods for using these compounds for inhibiting growth of cancer cells. Also provided herein are methods for using these compounds for treating a subject for hyperproliferative conditions, including without limitation the treatment of hematopoietic cancers.

1 Claim, 5 Drawing Sheets

FIG. 1

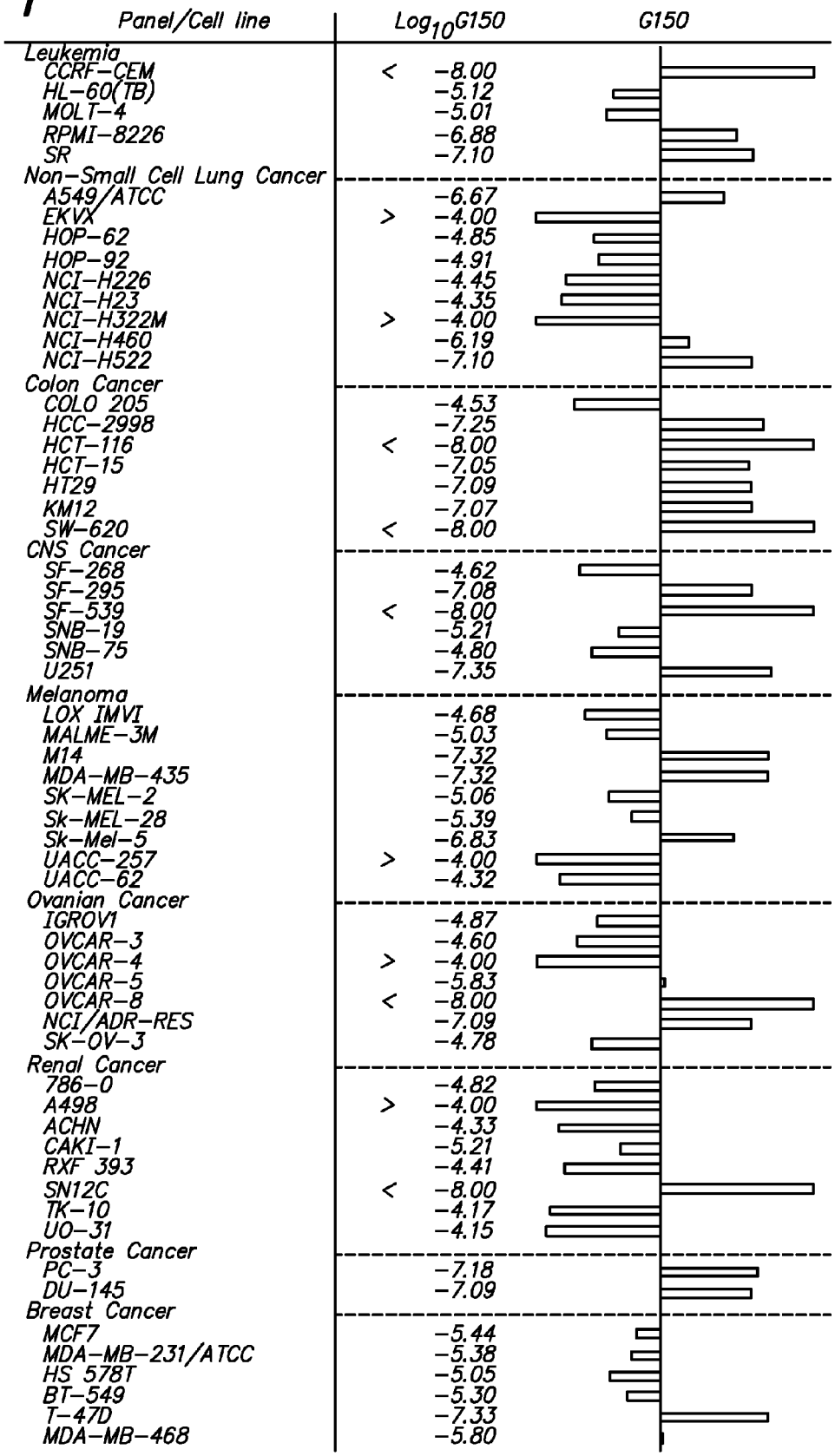

| Panel/Cell line | | Log₁₀GI50 | GI50 |
|---|---|---|---|
| Leukemia | | | |
| CCRF-CEM | < | -8.00 | |
| HL-60(TB) | | -5.12 | |
| MOLT-4 | | -5.01 | |
| RPMI-8226 | | -6.88 | |
| SR | | -7.10 | |
| Non-Small Cell Lung Cancer | | | |
| A549/ATCC | | -6.67 | |
| EKVX | > | -4.00 | |
| HOP-62 | | -4.85 | |
| HOP-92 | | -4.91 | |
| NCI-H226 | | -4.45 | |
| NCI-H23 | | -4.35 | |
| NCI-H322M | > | -4.00 | |
| NCI-H460 | | -6.19 | |
| NCI-H522 | | -7.10 | |
| Colon Cancer | | | |
| COLO 205 | | -4.53 | |
| HCC-2998 | | -7.25 | |
| HCT-116 | < | -8.00 | |
| HCT-15 | | -7.05 | |
| HT29 | | -7.09 | |
| KM12 | | -7.07 | |
| SW-620 | < | -8.00 | |
| CNS Cancer | | | |
| SF-268 | | -4.62 | |
| SF-295 | | -7.08 | |
| SF-539 | < | -8.00 | |
| SNB-19 | | -5.21 | |
| SNB-75 | | -4.80 | |
| U251 | | -7.35 | |
| Melanoma | | | |
| LOX IMVI | | -4.68 | |
| MALME-3M | | -5.03 | |
| M14 | | -7.32 | |
| MDA-MB-435 | | -7.32 | |
| SK-MEL-2 | | -5.06 | |
| SK-MEL-28 | | -5.39 | |
| SK-MEL-5 | | -6.83 | |
| UACC-257 | > | -4.00 | |
| UACC-62 | | -4.32 | |
| Ovarian Cancer | | | |
| IGROV1 | | -4.87 | |
| OVCAR-3 | | -4.60 | |
| OVCAR-4 | > | -4.00 | |
| OVCAR-5 | | -5.83 | |
| OVCAR-8 | < | -8.00 | |
| NCI/ADR-RES | | -7.09 | |
| SK-OV-3 | | -4.78 | |
| Renal Cancer | | | |
| 786-0 | | -4.82 | |
| A498 | > | -4.00 | |
| ACHN | | -4.33 | |
| CAKI-1 | | -5.21 | |
| RXF 393 | | -4.41 | |
| SN12C | < | -8.00 | |
| TK-10 | | -4.17 | |
| UO-31 | | -4.15 | |
| Prostate Cancer | | | |
| PC-3 | | -7.18 | |
| DU-145 | | -7.09 | |
| Breast Cancer | | | |
| MCF7 | | -5.44 | |
| MDA-MB-231/ATCC | | -5.38 | |
| HS 578T | | -5.05 | |
| BT-549 | | -5.30 | |
| T-47D | | -7.33 | |
| MDA-MB-468 | | -5.80 | |

ANTI-PROLIFERATIVE COMPOUNDS AND METHODS FOR USING THE SAME

GOVERNMENT RIGHTS

This invention was made with Government support under grant No. CA116606 awarded by the National Cancer Institute. The Government has certain rights in this invention.

CROSS REFERENCE TO RELATED APPLICATIONS

This application is a national stage application of PCT/US12/37936, filed May 15, 2012, which claims priority to U.S. Provisional Application Ser. No. 61/488,103, filed May 19, 2011, the disclosures of which are herein incorporated by reference in their entirety.

INTRODUCTION

Acute leukemia is a significant cause of morbidity and mortality and is of particular concern because it often affects children and young adults. Survival rates are particularly poor in the very young and the elderly. Although significant advances have been made in treating leukemia, high-risk acute lymphoblastic leukemia (ALL) and acute myeloid leukemia (AML) continue to pose significant therapeutic challenges.

Cytotoxic agents remain the standard of care for treatment of acute leukemia. Despite many attempts to improve treatments with new drug combinations, this approach has reached a point of diminishing returns since intensified chemotherapies contribute only marginal improvement in outcome and are associated with increasing toxicity. Thus, new therapeutics with improved outcomes and reduced toxicity are needed.

Leukemias, like all cancers, are caused by genetic aberrations that activate cellular oncogenes and inactivate tumor suppressor genes. These aberrations dictate the biological and clinical behaviors of leukemias and stratify them into low, intermediate, and high-risk categories. A significant subset of leukemias contains aberrations of the mixed lineage leukemia (MLL) gene, which is a frequent target for recurrent chromosomal translocations found in human acute leukaemias that may be characterized as either AML, ALL, or biphenotypic (mixed lineage) leukemia. Leukemias with chromosomal translocations involving the MLL gene are almost always classified as high-risk and receive intensified chemotherapy regimens. Although patients generally respond to treatment initially, there is a high-failure rate due to early relapse and recurrent disease. MLL translocation-associated leukemias, therefore, serve as a useful practical model for the isolation, validation and application of inhibitory compounds directed against high-risk cancers.

SUMMARY OF THE INVENTION

Disclosed herein are compounds which find use in inhibiting the proliferation of cancer cells, which include hematopoietic cancers, including lymphoma and leukemia cells, particularly including leukemia cells carrying a genetic abnormality in the MLL gene, e.g., an MLL chromosomal translocation. In other embodiments the cancer cells are solid tumors, for example, carcinomas, e.g. prostate cancer, colon cancer, etc. Compounds of interest include those set forth herein. Also provided herein are methods for using these compounds for inhibiting growth of such cells. Also provided herein are methods for using these compounds for treating a subject for hyperproliferative conditions. These compounds find use in a variety of applications in which inhibition of the growth of such cells is desired.

In some embodiments of the invention, pharmaceutical compositions are provided, which comprise an effective dose of a compound identified herein, which dose is effective in treating a subject with a hematopoietic hyperproliferative condition, including without limitation MLL translocation-associated leukemia; and which composition may further comprise a physiologically acceptable excipient.

The above summary is not intended to include all features and aspects of the present invention nor does it imply that the invention must include all features and aspects discussed in this summary.

All publications and patent applications mentioned in this specification are herein incorporated by reference to the same extent as if each individual publication or patent application was specifically and individually indicated to be incorporated by reference.

BRIEF DESCRIPTION OF THE DRAWINGS

FIG. 1. Mean graph representing the sensitivity of 60 human cell lines to compound 1. The vertical line at $GI_{50}$ (the drug concentration resulting in a 50% growth reduction) represents the mean response to 10 µM compound 1.

DEFINITIONS

Figure 2:
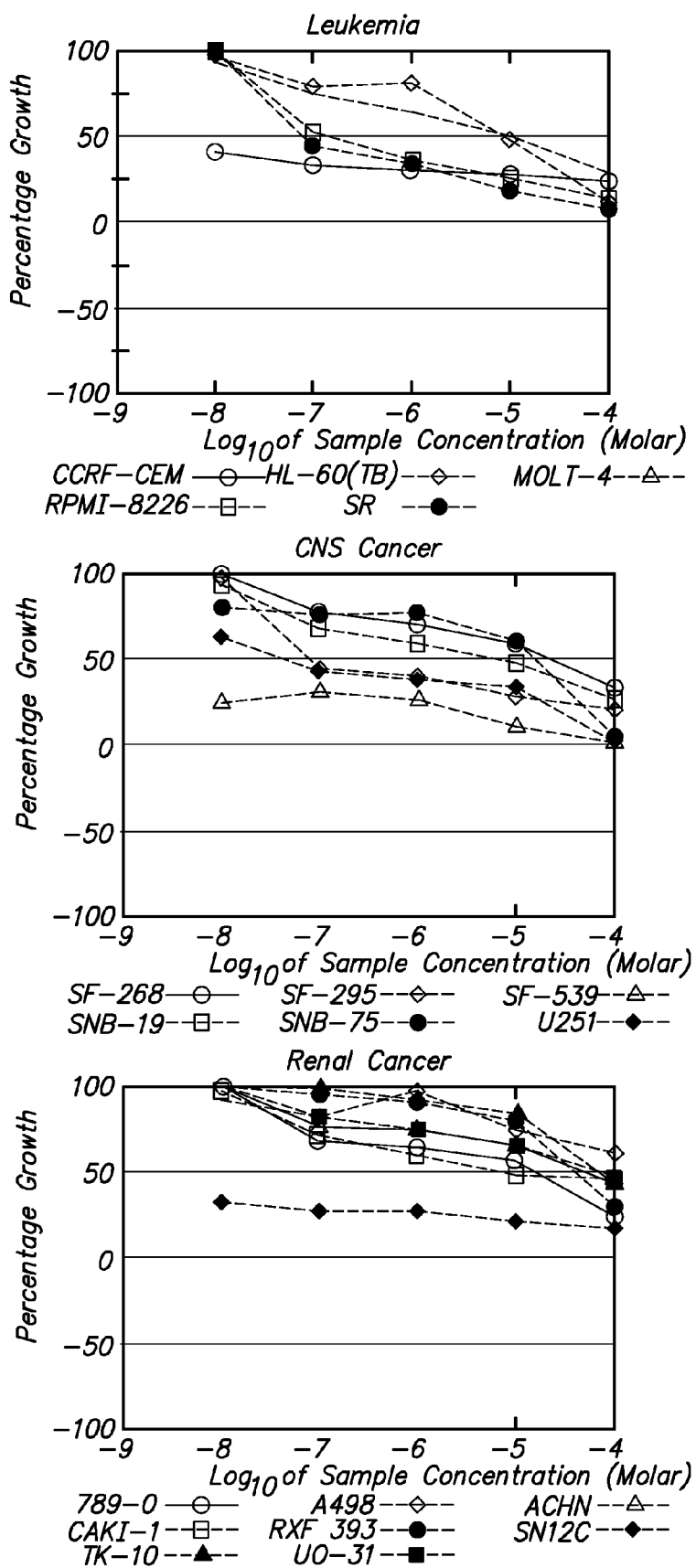
FIG. 2. Growth response of human cell lines grown for 2 days in the presence of increasing concentrations of compound 1.
Figure 2:
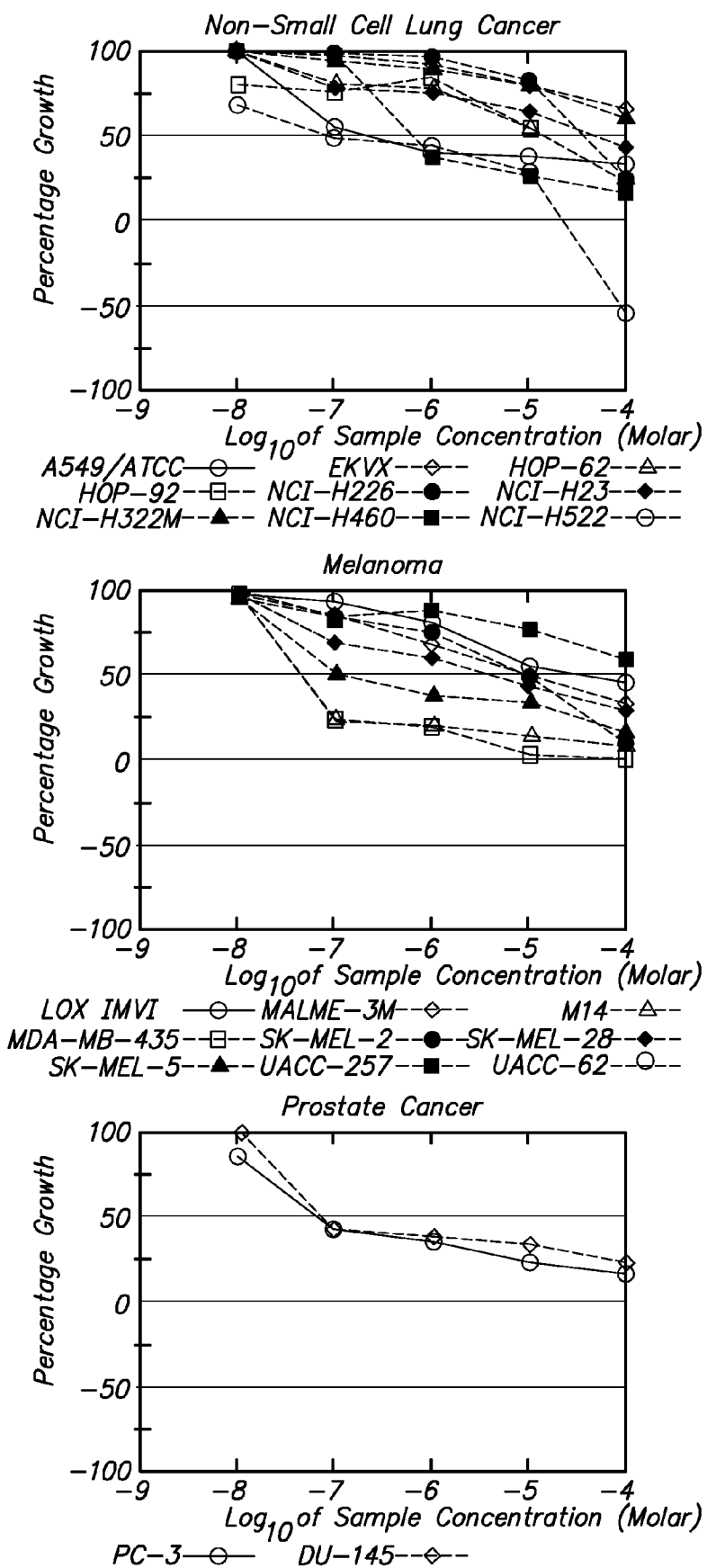
Figure 2:
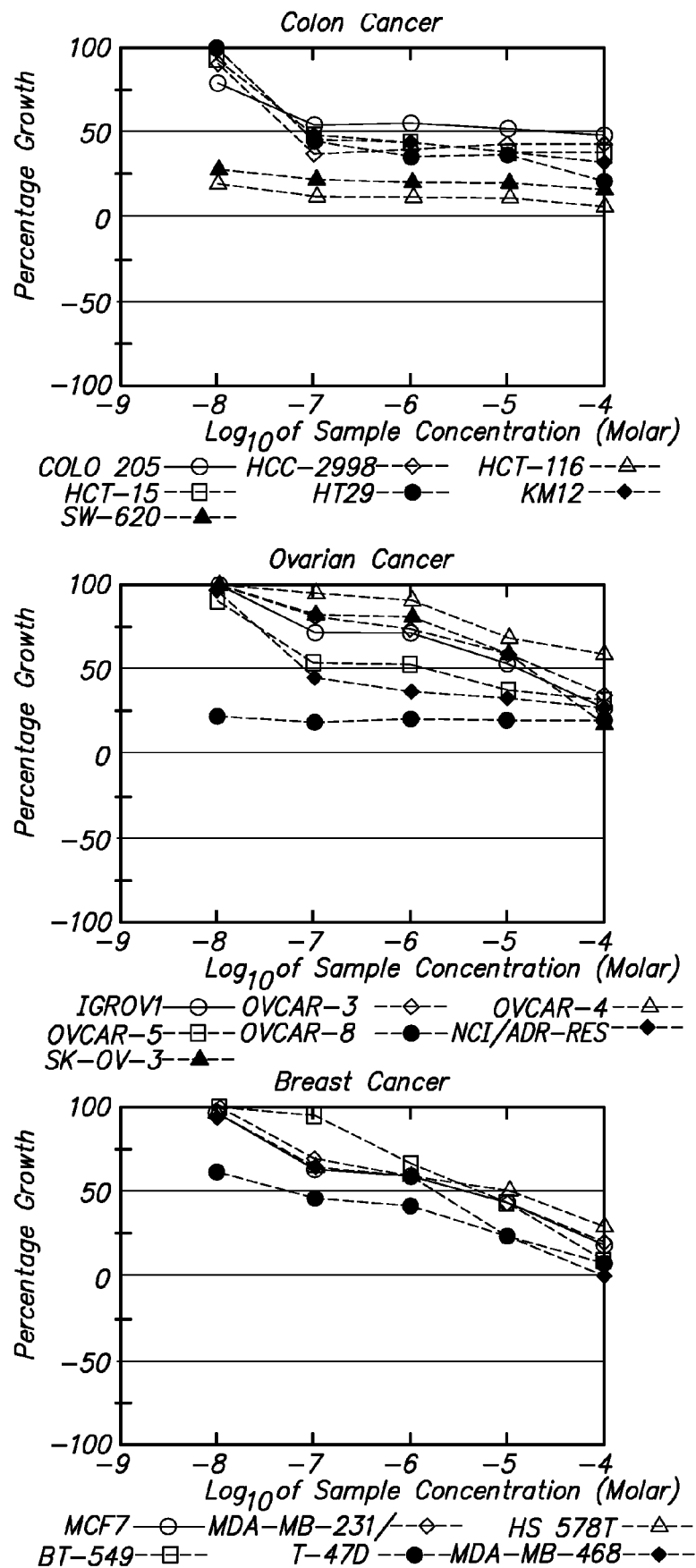

The term "in combination with" as used herein refers to uses where, for example, the first compound is administered during the entire course of administration of the second compound; where the first compound is administered for a period of time that is overlapping with the administration of the second compound, e.g. where administration of the first compound begins before the administration of the second compound and the administration of the first compound ends before the administration of the second compound ends; where the administration of the second compound begins before the administration of the first compound and the administration of the second compound ends before the administration of the first compound ends; where the administration of the first compound begins before administration of the second compound begins and the administration of the second compound ends before the administration of the first compound ends; where the administration of the second compound begins before administration of the first compound begins and the administration of the first compound ends before the administration of the second compound ends. As such, "in combination" can also refer to regimen involving administration of two or more compounds. "In combination with" as used herein also refers to administration of two or more compounds which may be administered in the same or different formulations, by the same of different routes, and in the same or different dosage form type.

The term "isolated compound" means a compound which has been substantially separated from, or enriched relative to, other compounds with which it occurs in nature or during chemical synthesis. Isolated compounds are usually at least about 80% pure, or at least about 90% pure, at least about 98% pure, or at least about 99% pure, by weight. The present invention is meant to encompass diastereomers as well as their racemic and resolved, enantiomerically pure forms and pharmaceutically acceptable salts thereof.

"Treating" or "treatment" of a condition or disease includes: (1) preventing at least one symptom of the conditions, i.e., causing a clinical symptom to not significantly develop in a mammal that may be exposed to or predisposed to the disease but does not yet experience or display symptoms of the disease, (2) inhibiting the disease, i.e., arresting or reducing the development of the disease or its symptoms, or (3) relieving the disease, i.e., causing regression of the disease or its clinical symptoms.

A "therapeutically effective amount" or "efficacious amount" means the amount of a compound that, when administered to a mammal or other subject for treating a disease, is sufficient to effect such treatment for the disease. The "therapeutically effective amount" will vary depending on the compound, the disease and its severity and the age, weight, etc., of the subject to be treated.

The terms "subject" and "patient" mean a mammal that may have a need for the pharmaceutical methods, compositions and treatments described herein. Subjects and patients thus include, without limitation, primate (including humans), canine, feline, ungulate (e.g., equine, bovine, swine (e.g., pig)), and other subjects. Humans and non-human animals having commercial importance (e.g., livestock and domesticated animals) are of particular interest.

"Mammal" means a member or members of any mammalian species, and includes, by way of example, canines; felines; equines; bovines; ovines; rodentia, etc. and primates, particularly humans. Non-human animal models, particularly mammals, e.g. primate, murine, lagomorpha, etc. may be used for experimental investigations.

The term "tumor," as used herein, refers to all neoplastic cell growth and proliferation, whether malignant or benign, and all pre-cancerous and cancerous cells and tissues.

The terms "cancer," "neoplasm," and "tumor" are used interchangeably herein to refer to cells which exhibit autonomous, unregulated growth, such that they exhibit an aberrant growth phenotype characterized by a significant loss of control over cell proliferation. In general, cells of interest for detection, analysis, classification, or treatment in the present application include precancerous (e.g., benign), malignant, pre-metastatic, metastatic, and non-metastatic cells. Examples of cancer include but are not limited to, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer.

As used herein, the term "cancer cell proliferation" refers to the proliferation of neoplastic cells that results in the growth of a tumor.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

As used herein, the terms "cancer recurrence" and "tumor recurrence," and grammatical variants thereof, refer to further growth of neoplastic or cancerous cells after diagnosis of cancer. Particularly, recurrence may occur when further cancerous cell growth occurs in the cancerous tissue. "Tumor spread," similarly, occurs when the cells of a tumor disseminate into local or distant tissues and organs; therefore tumor spread encompasses tumor metastasis.

The term "diagnosis" is used herein to refer to the identification of a molecular or pathological state, disease or condition, such as the identification of a molecular subtype of breast cancer, prostate cancer, or other type of cancer.

The term "prognosis" is used herein to refer to the prediction of the likelihood of cancer-attributable death or progression, including recurrence, metastatic spread, and drug resistance, of a neoplastic disease, such as lung, colon, skin or esophageal cancer. The term "prediction" is used herein to refer to the act of foretelling or estimating, based on observation, experience, or scientific reasoning. In one example, a physician may predict the likelihood that a patient will survive, following surgical removal of a primary tumor and/or chemotherapy for a certain period of time without cancer recurrence.

As used herein, the phrase "disease-free survival," refers to the lack of such tumor recurrence and/or spread and the fate of a patient after diagnosis, with respect to the effects of the cancer on the life-span of the patient. The phrase "overall survival" refers to the fate of the patient after diagnosis, despite the possibility that the cause of death in a patient is not directly due to the effects of the cancer. The phrases, "likelihood of disease-free survival", "risk of recurrence" and variants thereof, refer to the probability of tumor recurrence or spread in a patient subsequent to diagnosis of cancer, wherein the probability is determined according to the process of the invention.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The term "physiological conditions" is meant to encompass those conditions compatible with living cells, e.g., predominantly aqueous conditions of a temperature, pH, salinity, etc. that are compatible with living cells.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes both one and more than one such excipient, diluent, carrier, and adjuvant.

As used herein, a "pharmaceutical composition" is meant to encompass a composition suitable for administration to a subject, such as a mammal, especially a human. In general a "pharmaceutical composition" is preferably sterile, and free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal and the like.

As used herein, "pharmaceutically acceptable derivatives" of a compound of the invention include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs.

A "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Compounds included in the present compositions, that are acidic in nature may react with any number of inorganic and organic bases to form pharmaceutically acceptable base salts. Bases may include, for example, the mineral bases, such as NaOH and KOH, but one of skill in the art would appreciate that other bases may also be used. See Ando et al., Remington: The Science and Practice of Pharmacy, 20th ed. 700-720 (Alfonso R. Gennaro ed.), 2000.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

In some embodiments, the pharmaceutically acceptable addition salts of the compounds described herein may also exist as various solvates, such as, for example, with water, methanol, ethanol, dimethylformamide, and the like. Mixtures of such solvates may also be prepared. The source of such solvate may be from the solvent of crystallization, inherent in the solvent of preparation or crystallization, or adventitious to such solvent.

A "pharmaceutically acceptable solvate or hydrate" of a compound of the invention means a solvate or hydrate complex that is pharmaceutically acceptable and that possesses the desired pharmacological activity of the parent compound, and includes, but is not limited to, complexes of a compound of the invention with one or more solvent or water molecules, or 1 to about 100, or 1 to about 10, or one to about 2, 3 or 4, solvent or water molecules.

The terms "contact", "contacts", "contacting" have their normal meaning and refer to combining two or more entities (e.g., two proteins, a polynucleotide and a cell, a cell and a candidate agent, etc.). Contacting can occur in vitro, in situ or in vivo and is used interchangeably with "expose to", "exposed to", "exposing to."

As used herein, the terms "reduce", "decrease" and "inhibit" are used together because it is recognized that, in some cases, an observed activity can be reduced below the level of detection of a particular assay. As such, it may not always be clear whether the activity is "reduced" or "decreased" below a level of detection of an assay, or is completely "inhibited". As used herein, compounds which are "commercially available" may be obtained from standard commercial sources including Acros Organics (Geel Belgium), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hannover, Germany), Spectrum Quality Product, Inc. (New Brunswick, N.J.), TCI America (Portland Oreg.), Trans World Chemicals, Inc. (Rockville Md.), Wako Chemicals USA, Inc. (Richmond Va.); Molecular Probes (Eugene, Oreg.); Invitrogen (Carlsbad, Calif.), Applied Biosystems, Inc. (Foster City, Calif.), Glen Research (Sterling, Va.), Biosearch Technologies (Novato, Calif.), Anaspec (Fremont, Calif.) and Berry & Associates (Dexter, Mich.).

As used herein, "suitable conditions" for carrying out a synthetic step are explicitly provided herein or may be discerned by reference to publications directed to methods used in synthetic organic chemistry. The reference books and treatise set forth above that detail the synthesis of reactants useful in the preparation of compounds of the present invention, will also provide suitable conditions for carrying out a synthetic step according to the present invention.

As used herein, "methods known to one of ordinary skill in the art" may be identified through various reference books and databases. Suitable reference books and treatise that detail the synthesis of reactants useful in the preparation of compounds of the present invention, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A.

Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services.

"Stable compound" and "stable structure" are meant to indicate a compound that is sufficiently robust to survive isolation to a useful degree of purity from a reaction mixture, and formulation into an efficacious therapeutic agent.

As used herein, the term "linker" or "linkage" or "linking group" refers to a linking moiety that connects two groups and has a backbone of 20 atoms or less in length. A linker or linkage may be a covalent bond that connects two groups or a chain of between 1 and 20 atoms in length, for example of about 1, 2, 3, 4, 5, 6, 8, 10, 12, 14, 16, 18 or 20 carbon atoms in length, where the linker may be linear, branched, cyclic or a single atom. In certain cases, one, two, three, four or five or more carbon atoms of a linker backbone may be optionally substituted with a sulfur, nitrogen or oxygen heteroatom. The bonds between backbone atoms may be saturated or unsaturated, usually not more than one, two, or three unsaturated bonds will be present in a linker backbone. The linker may include one or more substituent groups, for example with an alkyl, aryl or alkenyl group. A linker may include, without limitations, oligo(ethylene glycol); ethers, thioethers, tertiary amines, alkyls, which may be straight or branched, e.g., methyl, ethyl, n-propyl, 1-methylethyl (iso-propyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution. The term lower alkyl will be used herein as known in the art to refer to an alkyl, straight, branched or cyclic, of from about 1 to 6 carbons. It will be understood by those skilled in the art, with respect to any group containing one or more substituents, that such groups are not intended to introduce any substitution or substitution patterns that are sterically impractical, synthetically non-feasible and/or inherently unstable.

When describing the compounds, pharmaceutical compositions containing such compounds and methods of using such compounds and compositions, the following terms have the following meanings unless otherwise indicated. It should also be understood that any of the moieties defined forth below may be unsubstituted or substituted with a variety of substituents, and that the respective definitions are intended to include both unsubstituted and substituted moieties within their scope.

"Acyl" refers to a —C(O)R group, where R is hydrogen, alkyl, alkenyl, cycloalkyl, heterocycloalkyl, aryl, arylalkyl, heteroalkyl, heteroalkenyl, or heteroaryl as defined herein. Representative examples include, but are not limited to, formyl, acetyl, cyclohexylcarbonyl, cyclohexylmethylcarbonyl, benzoyl, benzylcarbonyl and the like.

"Acylamino" refers to a —NR'C(O)R group, where R' is hydrogen, alkyl, cycloalkyl, heterocycloalkyl, aryl, arylalkyl, heteroalkyl, heteroaryl, heteroarylalkyl and R is hydrogen, alkyl, alkoxy, cycloalkyl, heterocycloalkyl, aryl, arylalkyl, heteroalkyl, heteroaryl or heteroarylalkyl, as defined herein. Representative examples include, but are not limited to, formylamino, acetylamino, cyclohexylcarbonylamino, cyclohexylmethyl-carbonylamino, benzoylamino, benzylcarbonylamino and the like.

"Acyloxy" refers to the group —OC(O)H, —OC(O)-alkyl, —OC(O)-aryl or —OC(O)— cycloalkyl.

"Aliphatic" refers to hydrocarbyl organic compounds or groups characterized by a straight, branched or cyclic arrangement of the constituent carbon atoms and an absence of aromatic unsaturation. Aliphatics include, without limitation, alkyl, alkylene, alkenyl, alkynyl and alkynylene. Lower aliphatic groups typically have from 1 or 2 to 6 or 12 carbon atoms.

"Alkenyl" refers to monovalent olefinically unsaturated hydrocarbyl groups having up to about 11 carbon atoms, such as from 2 to 8 carbon atoms, and including from 2 to 6 carbon atoms, which can be straight-chained or branched and having at least 1 and including from 1 to 2 sites of olefinic unsaturation. Particular alkenyl groups include ethenyl (—CH═CH2), n-propenyl (—CH2CH═CH2), isopropenyl (—C(CH3)═CH2), vinyl and substituted vinyl, and the like.

"Alkoxy" refers to the group —O-alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Alkoxycarbonyl" refers to a radical —C(O)-alkoxy where alkoxy is as defined herein.

"Alkoxycarbonylamino" refers to the group —NRC(O)OR' where R is hydrogen, alkyl, aryl or cycloalkyl, and R' is alkyl or cycloalkyl.

"Alkyl" refers to monovalent saturated aliphatic hydrocarbyl groups particularly having up to about 12 or 18 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "alkyl" also includes "cycloalkyls" as defined herein.

"Alkylene" refers to divalent saturated aliphatic hydrocarbyl groups particularly having up to about 12 or 18 carbon atoms and more particularly 1 to 6 carbon atoms which can be straight-chained or branched. This term is exemplified by groups such as methylene (—CH2-), ethylene (—CH2CH2-), the propylene isomers (e.g., —CH2CH2CH2- and —CH(CH3)CH2-) and the like.

"Alkynyl" refers to acetylenically unsaturated hydrocarbyl groups particularly having up to about 12 or 18 carbon atoms and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—CH2C≡CH), and the like.

"Amino" refers to the radical —NH2.

"Aminocarbonyl" refers to the group —C(O)NRR where each R is independently hydrogen, alkyl, aryl or cycloalkyl, or where the R groups are joined to form an alkylene group.

"Aminocarbonylamino" refers to the group —NRC(O)NRR where each R is independently hydrogen, alkyl, aryl or cycloalkyl, or where two R groups are joined to form an alkylene group.

"Aminocarbonyloxy" refers to the group —OC(O)NRR where each R is independently hydrogen, alkyl, aryl or cycloalky, or where the R groups are joined to form an alkylene group.

"Aralkyl" or "arylalkyl" refers to an alkyl group, as defined above, substituted with one or more aryl groups, as defined above.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some cases, an aryl group includes from 6 to 14 carbon atoms.

"Aryloxy" refers to —O-aryl groups wherein "aryl" is as defined herein.

"Azido" refers to a —N3 group.

"Carbonyl" refers to —C(O)— groups, for example, a carboxy, an amido, an ester, a ketone, or an acyl substituent.

"Carboxyl" refers to a —C(O)OH group

"Cyano" refers to a —CN group.

"Cycloalkenyl" refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like.

"Heterocycloalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl and morpholinyl.

"Halogen" or "halo" refers to fluoro, chloro, bromo and iodo.

"Hetero" when used to describe a compound or a group present on a compound means that one or more carbon atoms in the compound or group have been replaced by, for example, a nitrogen, oxygen, or sulfur heteroatom. Hetero may be applied to any of the hydrocarbyl groups described above such as alkyl, e.g. heteroalkyl, cycloalkyl, e.g. heterocycloalkyl, aryl, e.g. heteroaryl, cycloalkenyl, e.g., heterocycloalkenyl, cycloheteroalkenyl, e.g., heterocycloheteroalkenyl and the like having from 1 to 5, and particularly from 1 to 3 heteroatoms. A heteroatom is any atom other than carbon or hydrogen and is typically, but not exclusively, nitrogen, oxygen, sulfur, phosphorus, boron, chlorine, bromine, or iodine.

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. The heteroaryl group can be a 5-20 membered heteroaryl, or 5-10 membered heteroaryl. Particular heteroaryl groups are those derived from thiophen, pyrrole, benzothiophene, benzofuran, indole, pyridine, quinoline, imidazole, oxazole and pyrazine.

The following ring systems are examples of the heterocyclic (whether substituted or unsubstituted) radicals denoted by the term "heteroaryl": thienyl, furyl, pyrrolyl, pyrrolidinyl, imidazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, oxazinyl, triazinyl, thiadiazinyl tetrazolo, 1,5-[b]pyridazinyl and purinyl, as well as benzo-fused derivatives, for example, benzoxazolyl, benzthiazolyl, benzimidazolyl and indolyl.

Substituents for the above optionally substituted heteroaryl rings include from one to three halo, trihalomethyl, amino, protected amino, amino salts, mono-substituted amino, di-substituted amino, carboxy, protected carboxy, carboxylate salts, hydroxy, protected hydroxy, salts of a hydroxy group, lower alkoxy, lower alkylthio, alkyl, substituted alkyl, cycloalkyl, substituted cycloalkyl, (cycloalkyl)alkyl, substituted (cycloalkyl)alkyl, phenyl, substituted phenyl, phenylalkyl, and (substituted phenyl)alkyl. Substituents for the heteroaryl group are as heretofore defined, or in the case of trihalomethyl, can be trifluoromethyl, trichloromethyl, tribromomethyl, or triiodomethyl. As used in conjunction with the above substituents for heteroaryl rings, "lower alkoxy" means a C1 to C4 alkoxy group, similarly, "lower alkylthio" means a C1 to C4 alkylthio group.

"Heterocycle" refers to organic compounds that contain a ring structure containing atoms in addition to carbon, such as sulfur, oxygen or nitrogen, as part of the ring. They may be either simple aromatic rings or non-aromatic rings. Examples include azoles, morpholine, piperazine, pyridine, pyrimidine and dioxane. The maximum number of heteroatoms in a stable, chemically feasible heterocyclic ring, whether it is aromatic or non aromatic, is determined by factors such as, the size of the ring, the degree of unsaturation and the valence of the heteroatoms. In general, a heterocyclic ring may have one to four heteroatoms so long as the heteroaromatic ring is chemically feasible and stable.

"Hydroxyl" refers to a —OH group.

"Stereoisomer" as it relates to a given compound refers to another compound having the same molecular formula, wherein the atoms making up the other compound differ in the way they are oriented in space, but wherein the atoms in the other compound are like the atoms in the given compound with respect to which atoms are joined to which other atoms (e.g. an enantiomer, a diastereomer, or a geometric isomer). See for example, Morrison and Boyd, Organic Chemistry, 1983, 4th ed., Allyn and Bacon, Inc., Boston, Mass., p. 123.

"Substituted" refers to a group in which one or more hydrogen atoms are each independently replaced with the same or different substituent(s). "Substituted" groups particularly refer to groups having 1 or more substituents, for instance from 1 to 5 substituents, and particularly from 1 to 3 substituents, selected from the group consisting of acyl, acylamino, acyloxy, alkoxy, alkoxycarbonyl, alkoxycarbonylamino, amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, thioaryloxy, thioketo, thiol, alkyl-S(O)—, aryl-S(O)—, alkyl-S(O)$_2$— and aryl-S(O)$_2$. Substituents of interest may include, but are not limited to, —X, —R8 (with the proviso that R8 is not hydrogen), —O—, =O, —OR8, —SR8, —S—, =S, —NR8R9, =NR8, —CX3, —CF3, —CN, —OCN, —SCN, —NO, —NO2, =N2, —N3, —S(O)2O—, —S(O)2OH, —S(O)2R8, —OS(O2)O—, —OS(O)2R8, —P(O)(O—)2, —P(O)(OR8)(O—), —OP(O)(OR8)(OR9), —C(O)R8, —C(S)R8, —C(O)OR8, —C(O)NR8R9, —C(O)O—, —C(S)OR8, —NR1 OC(O)NR8R9, vNR10C(S)NR8R9, —NR11C(NR10)NR8R9 and —C(NR10)NR8R9, where each X is independently a halogen and R8 is an alkyl, an alkenyl, an alkynyl, a heterocycle or an aryl.

"Sulfonyl" refers to the group —SO2-. Sulfonyl includes, for example, methyl-SO2-, phenyl-SO2-, and alkylamino-SO2-.

"Sulfinyl" refers to the group —C(O)—.

"Thioalkoxy" refers to the group —S-alkyl.

"Thioaryloxy" refers to the group —S-aryl.

"Thioketo" refers to the group =S.

"Thiol" refers to the group —SH.

"Thio" refers to the group —S—. Thio includes, for example, thioalkoxy, thioaryloxy, thioketo and thiol.

"Optional" or "optionally" means that the subsequently described event, circumstance, feature or element may, but need not, occur, and that the description includes instances where the event or circumstance occurs and instances in which it does not. For example, "heterocyclo group optionally mono- or di-substituted with an alkyl group" means that the alkyl may, but need not, be present, and the description includes situations where the heterocyclo group is mono- or disubstituted with an alkyl group and situations where the heterocyclo group is not substituted with the alkyl group.

As to any of the groups disclosed herein which contain one or more substituents, it is understood, of course, that such groups do not contain any substitution or substitution patterns which are sterically impractical and/or synthetically nonfeasible. In addition, the subject compounds include all stereochemical isomers arising from the substitution of these compounds.

Compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see, e.g., the discussion in Chapter 4 of "Advanced Organic Chemistry", 4th edition J. March, John Wiley and Sons, New York, 1992).

DETAILED DESCRIPTION OF THE EMBODIMENTS

As summarized above, aspects of the invention include anti-proliferative compounds that inhibit the growth of cancer cells, e.g. leukemia cells, carcinomas, etc., upon contact with a cell or components thereof. In some embodiments, the types of cells upon which the subject compounds exhibit activity are leukemia cells carrying genetic aberrations in the MLL gene, e.g., MLL translocations. By inhibiting cell growth is meant that the growth of the cells is decreased by at least 10%, such as at least 20%, at least 30%, at least 40%, at least 50%, at least 60%, at least 70%, at least 80%, at least 90%, at least 95%, or even more, relative to a control, i.e., growth of comparable cells (such as a clone, cell from the same tissue, etc.) not contacted with the compound of interest.

The present disclosure also provides a method of using the subject compound(s) for inhibiting the growth of cancer cells, e.g. leukemia cells, carcinomas, etc. The present disclosure also provides a method of identifying a compound that inhibits growth of cancer cells. For example, the method may use a leukemia cell line that includes a genetic aberration in the MLL gene, e.g., a MLL translocation.

Methods of the invention include contacting a cell, e.g. a cancer cell, with an effective dose of a compound described herein, to inhibit the growth of the cells. Methods of the invention include in vitro and in vivo methods, the methods comprising contacting a population of target cells with an effective dose of a compound of the invention. In vitro cultures include, for example, models of MLL translocation-associated leukemias, models of tumors, for example for pre-clinical testing purposes, compound screening, and the like. In vivo cells include animal models and human patients having an undesirable hyperproliferative condition, e.g. lymphoma, leukemia, etc. for which a reduction in the growth of targeted cells is desired, e.g. to treat or prevent leukemia, such as MLL translocation-associated leukemia.

In certain embodiments, the subject compounds inhibit growth of leukemia cells (e.g., human cell lines representative of high-risk B-ALL, including without limitation RS411, HB, MV411, SEM and KP-R-YL), which inhibition may be measured, for example, by a cell proliferation assay that measures the absorbance or fluorescence of a marker of the density of cells in culture, relative to a control (e.g., cells representative of low-risk ALL), i.e., compounds of the invention show signals that are reduced by at least 10%, such as at least 20%, at least 30%, at least 40%, at least 50%, at least 60%, at least 70%, at least 80%, at least 90%, at least 95%, or even more, relative to a control signal. In particular embodiments, compounds of the invention inhibit growth of leukemia cells by a cell proliferation assay with an $IC_{50}$ value of 10 µM or less, such as 3 µM or less, 1 µM or less, 300 nM or less, 100 nM or less, 30 nM or less, 10 nM or less, 3 nM or less, 1 nM or less, or even smaller.

In certain embodiments, the subject compounds inhibit tumorigenic colony formation and/or growth of cancer stem cells which may be measured, for example, in a mouse model of AML induced by MLL, where the leukemic colony forming cells (CFCs) represent stem cells (LSCs), i.e., compounds of the invention show signals in CFC assays that are reduced by at least 10%, such as at least 20%, at least 30%, at least 40%, at least 50%, at least 60%, at least 70%, at least 80%, at least 90%, at least 95%, or even more, relative to a control signal. In particular embodiments, compounds of the invention inhibit the ability of AML cells (e.g., induced by MLL-AF9 or MLL-AF10 to form CFCs) with an $IC_{50}$ value of 10 uM or less, such as 3 µM or less, 1 µM or less, 300 nM or less, 100 nM or less, 30 nM or less, 10 nM or less, 3 nM or less, 1 nM or less, or even smaller.

In certain embodiments, the subject compounds inhibit growth of cancer cells in vivo which may be measured, for example, in a xenograft model of human B-ALL, i.e., compounds of the invention show signals that are reduced by at least 10%, such as at least 20%, at least 30%, at least 40%, at least 50%, at least 60%, at least 70%, at least 80%, at least 90%, at least 95%, or even more, relative to a control signal. In particular embodiments, compounds of the invention inhibit growth of leukemia cells by a cell proliferation assay with an IC50 value of 10 uM or less, such as 3 uM or less, 1 uM or less, 300 nM or less, 100 nM or less, 30 nM or less, 10 nM or less, 3 nM or less, 1 nM or less, or even smaller.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that and in the appended claims, the singular forms "a," "an," and "the" include plural referents unless the context clearly dictates otherwise. Thus, for example, reference to "a method" includes a plurality of such methods and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the chemical groups represented by the variables are specifically embraced by the present invention and are disclosed herein just as if each and every combination was individually and explicitly disclosed, to the extent that such combinations embrace compounds that are stable compounds (i.e., compounds that can be isolated, characterized, and tested for biological activity). In addition, all sub-combinations of the chemical groups listed in the embodiments describing such variables are also specifically embraced by the present invention and are disclosed herein just as if each and every such sub-combination of chemical groups was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Compositions

Provided herein are anti-proliferative compounds that may be used to inhibit the growth of cancer cells, including without limitation leukemia cells carrying a genetic aberration in the MLL gene. These compounds can be incorporated into a variety of formulations for therapeutic administration by a variety of routes. More particularly, the compounds disclosed herein can be formulated into pharmaceutical compositions by combination with appropriate, pharmaceutically acceptable carriers, diluents, excipients and/or adjuvants.

In certain embodiments, the subject compounds include a substituent that contributes to optical isomerism and/or stereo isomerism of a compound. Salts, solvates, hydrates, and prodrug forms of a compound are also of interest. All such forms are embraced by the present invention. Thus the compounds described herein include salts, solvates, hydrates, prodrug and isomer forms thereof, including the pharmaceutically acceptable salts, solvates, hydrates, prodrugs and isomers thereof. In certain embodiments, a compound may be a metabolized into a pharmaceutically active derivative.

The following are examples of compounds of the invention.

Aryl-Amidophenyls

In certain embodiments, the subject compounds are aryl-amidophenyls, e.g., compounds that include an aryl group (including without limitation a 2-pyridyl, a 3-pyridyl or a 4-pyridyl group) linked to a phenyl group via an amide bond containing linker (e.g., —$(CH_2)_n$—NHCO— or —$(CH_2)_n$—CONH— where n is 0, 1, 2 or 3), where the phenyl group is further substituted (e.g., substituted at the position para to the amide) with a sulfonyl-phenyl (—$SO_2$-Ph) containing substituent, such as a -hetereocyclyl-$(CH_2)_n$—$SO_2$-Ph or —$(CH_2)_n NHSO_2$-Ph. The aryl-amidophenyl compounds may be optionally further substituted.

In some embodiments, an aryl-amidophenyl compound of the invention is of the structure of Formula (I):

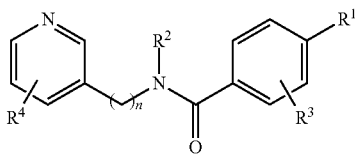
(I)

where n is 0, 1, 2 or 3;

$R^2$ is hydrogen, an alkyl (e.g., a lower alkyl) or an aryl;

$R^3$ and $R^4$ are each one or more groups, each $R^3$ and $R^4$ independently selected from hydrogen, acyl, acylamino, acyloxy, alkoxy, alkoxycarbonyl, amino, alkyl, aryl, aryloxy, azido, carboxyl, cyano, halogen, hydroxyl, nitro, thiol, sulfone;

where m is 0, 1, 2 or 3;

X is oxygen, sulfur or nitrogen;

and where in some such compounds, $R_1$ is

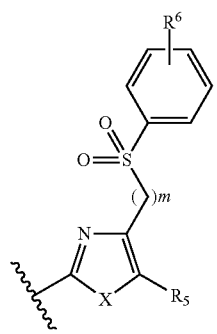

and in other such compounds, $R_1$ is:

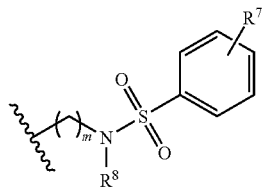

where $R^5$ is hydrogen, an aryl or an alkyl;

$R^8$ is hydrogen, an alkyl (e.g., a lower alkyl) or an aryl; and $R^6$ and $R^7$ are each one or more groups, each $R^6$ and $R^7$ independently selected from hydrogen, acyl, acylamino, acyloxy, alkoxy, alkoxycarbonyl, amino, alkyl, aryl, aryloxy, azido, carboxyl, cyano, halogen, hydroxyl, nitro, thiol, and sulfone.

In some embodiments, in Formula I, n is 0 or 1. In some embodiments, in Formula I, $R^2$ is hydrogen. In some embodiments, in Formula I, $R^3$ is hydrogen. In some embodiments, in Formula I, $R^4$ is hydrogen. In some embodiments, in Formula I, $R^6$ is hydrogen. In some embodiments, in Formula I, $R^7$ is hydrogen. In some embodiments, in Formula I, m is 1. In some embodiments, in Formula I, X is oxygen. In some embodiments, in Formula I, $R^5$ is a lower alkyl (e.g., methyl). In some embodiments, in Formula I, $R^8$ is hydrogen or a phenyl.

In some embodiments, in Formula I, $R^1$ is described by the structure:

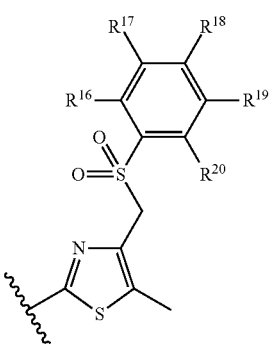

where $R^{16}$ to $R^{20}$ are independently selected from hydrogen, acyl, acylamino, acyloxy, alkoxy, alkoxycarbonyl, amino, alkyl, aryl, aryloxy, azido, carboxyl, cyano, halogen, hydroxyl, nitro, thiol, and sulfone. In certain embodiments, $R^{16}$, $R^{17}$, $R^{19}$ and $R^{20}$ are each hydrogen and $R^{18}$ is an alkyl, such as a lower alkyl (e.g., methyl).

In some embodiments, in Formula I, $R^1$ is described by the structure:

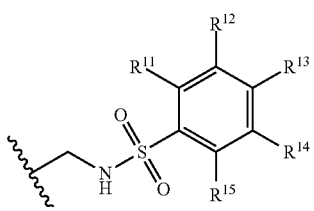

where $R^{11}$ to $R^{15}$ are independently selected from hydrogen, acyl, acylamino, acyloxy, alkoxy, alkoxycarbonyl, amino, alkyl, aryl, aryloxy, azido, carboxyl, cyano, halogen, hydroxyl, nitro, thiol, and sulfone. In some embodiments, one or more (such as 2, 3, 4 or more) of $R^{11}$ to $R^{15}$ is independently an alkyl (e.g., a lower alkyl), where the alkyl may be substituted (e.g., a halo-substituted alkyl such as trifluoromethyl) or unsubstituted. In certain embodiments, $R^{13}$ is hydrogen and $R^{11}$, $R^{12}$, $R^{14}$ and $R^{15}$ are each independently an alkyl substituent. In certain embodiments, $R^{12}$ is an alkyl (e.g., a trifluoromethyl) and $R^{11}$, $R^{13}$, $R^{14}$ and $R^{15}$ are each hydrogen.

In some embodiments, a compound is of the structure of Formula I where n is 0 or 1; m is 1; $R^2$, $R^3$ and $R^4$ are hydrogen; X is oxygen; and $R^5$ is a lower alkyl (e.g., methyl).

In certain embodiments, an aryl-amidophenyl compound is described by the structure of one of the following compounds:

Compound 1

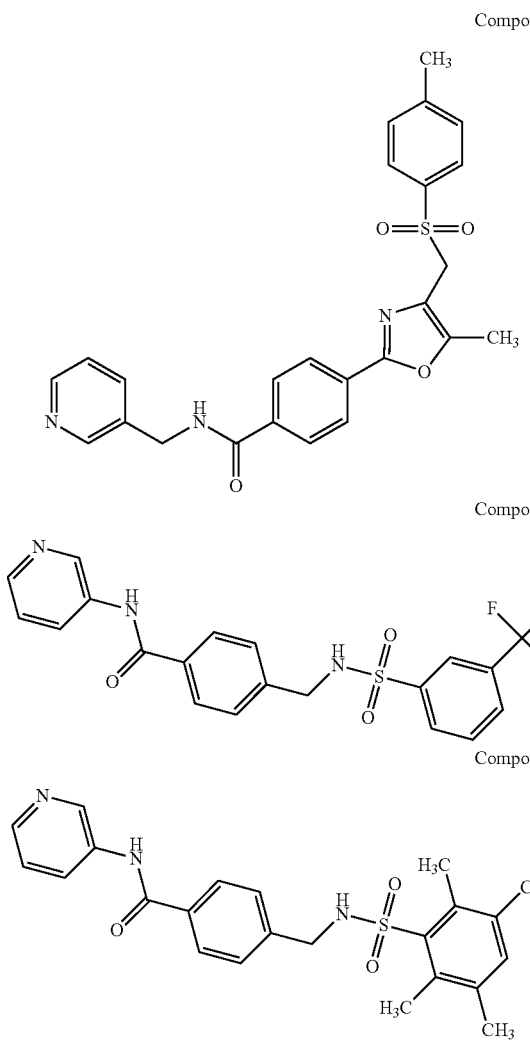

Compound 2

Compound 3

Compound Formulae

In some embodiments of the invention, the compound or a salt thereof of the invention has the structure:

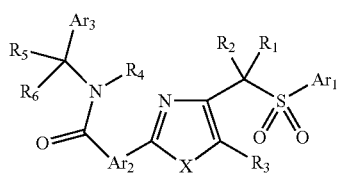

where $R_1$, $R_2$, $R_5$, $R_6$ are independently H, alkyl, alkynyl, cycloalkyl, alkylcycloalkyl, aryl or alkylaryl;

$R_1$ to $R_2$ and $R_5$ to $R_6$ can be joined to form a 3 to 5 member cycloalkyl rings;

$R_3$, $R_4$ are independently H, alkyl, cycloalkyl, alkylcycloalkyl, aryl or alkylaryl;

$Ar_1$, $Ar_2$, $Ar_3$ are independently substituted aryl or substituted heteroaryl; and X is oxygen or sulfur.

In some embodiments of the invention, the compound or a salt thereof of the invention has the structure:

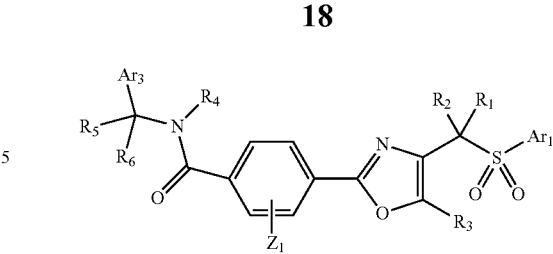

where $R_1$, $R_2$, $R_5$, $R_6$ are independently H, alkyl, alkynyl, cycloalkyl, alkylcycloalkyl, aryl or alkylaryl;

$R_1$ to $R_2$ and $R_5$ to $R_6$ can be joined to form a 3 to 5 member cycloalkyl rings;

$R_3$, $R_4$ are independently H, alkyl, cycloalkyl, alkylcycloalkyl, aryl or alkylaryl;

$Ar_1$, $Ar_3$ are independently substituted aryl or substituted heteroaryl;

$Z_1$ are 1 to 4 substituents comprising H, alkyl, cyclopropyl, alkynyl, halogens, hydroxyl, alkoxides, alkylsulfones, alkyl sulfides, cyano, nitro, trifluoromethyl, mono alkyl substituted carboxyamide, alkyl carboxyl ester, amino, monoalkyl amino, dialkyl amino, aminosulfonyl, sulfonylamino, or a 5 or 6 membered appended ring comprising carbon or carbon and one or two oxygen or nitrogen atoms.

In some embodiments of the invention, the compound or a salt thereof of the invention has the structure:

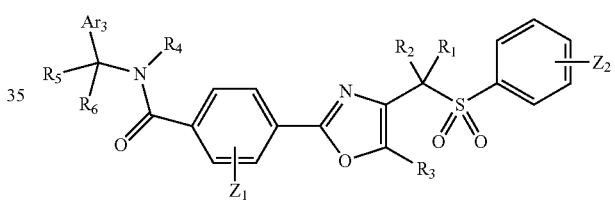

where $R_1$, $R_2$, $R_5$, $R_6$ are independently H, alkyl, alkynyl, cycloalkyl, alkylcycloalkyl, aryl or alkylaryl;

$R_1$ to $R_2$ and $R_5$ to $R_6$ can be joined to form a 3 to 5 member cycloalkyl rings;

$R_3$, $R_4$ are independently H, alkyl, cycloalkyl, alkylcycloalkyl, aryl or alkylaryl;

$Ar_3$ are independently substituted aryl or substituted heteroaryl;

$Z_1$ are 1 to 4 substituents comprising H, alkyl, cyclopropyl, alkynyl, halogens, hydroxyl, alkoxides, alkylsulfones, alkyl sulfides, cyano, nitro, trifluoromethyl, mono alkyl substituted carboxyamide, alkyl carboxyl ester, amino, monoalkyl amino, aminosulfonyl, sulfonylamino, dialkyl amino or a 5 or 6 membered appended ring comprising carbon or carbon and one or two oxygen or nitrogen atoms; and $Z_2$ are 1 to 5 substituents comprising H, alkyl, cyclopropyl, alkynyl, halogens, hydroxyl, alkoxides, alkylsulfones, alkyl sulfides, cyano, nitro, trifluoromethyl, mono alkyl substituted carboxyamide, alkyl carboxyl ester, amino, monoalkyl amino, dialkyl amino, aminosulfonyl, sulfonylamino, or a 5 or 6 membered appended ring comprising carbon or carbon and one or two oxygen or nitrogen atoms.

In some embodiments of the invention, the compound or a salt thereof of the invention has the structure:

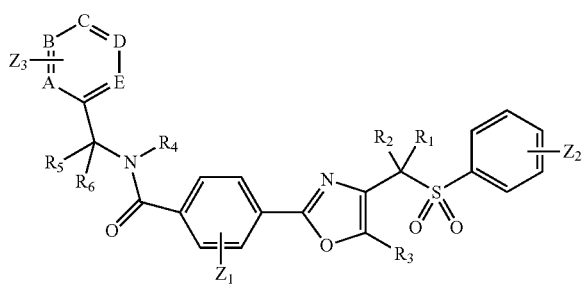

where $R_1$, $R_2$, $R_5$, $R_6$ are independently H, alkyl, alkynyl, cycloalkyl, alkylcycloalkyl, aryl or alkylaryl;

$R_1$ to $R_2$ and $R_5$ to $R_6$ can be joined to form a 3 to 5 member cycloalkyl rings;

$R_3$, $R_4$ are independently H, alkyl, cycloalkyl, alkylcycloalkyl, aryl or alkylaryl;

$Z_1$ are 1 to 4 substituents comprising H, alkyl, cyclopropyl, alkynyl, halogens, hydroxyl, alkoxides, alkylsulfones, alkyl sulfides, cyano, nitro, trifluoromethyl, mono alkyl substituted carboxyamide, alkyl carboxyl ester, amino, monoalkyl amino, aminosulfonyl, sulfonylamino, dialkyl amino or a 5 or 6 membered appended ring comprising carbon or carbon and one or two oxygen or nitrogen atoms;

$Z_2$ are 1 to 5 substituents comprising H, alkyl, cyclopropyl, alkynyl, halogens, hydroxyl, alkoxides, alkylsulfones, alkyl sulfides, cyano, nitro, trifluoromethyl, mono alkyl substituted carboxyamide, alkyl carboxyl ester, amino, monoalkyl amino, aminosulfonyl, sulfonylamino, dialkyl amino or a 5 or 6 membered appended ring comprising carbon or carbon and one or two oxygen or nitrogen atoms;

$Z_3$ are 1 to 5 substituents comprising H, alkyl, cyclopropyl, alkynyl, halogens, hydroxyl, alkoxides, alkylsulfones, alkyl sulfides, cyano, nitro, trifluoromethyl, mono alkyl substituted carboxyamide, alkyl carboxyl ester, amino, monoalkyl amino, aminosulfonyl, sulfonylamino, dialkyl amino or a 5 or 6 membered appended ring comprising carbon or carbon and one or two oxygen or nitrogen atoms; and A, B, C, D and E are independently substituted carbons or independently substituted carbons and 1 to 3 nitrogen atoms.

In some embodiments of the invention, the compound or a salt thereof of the invention has the structure:

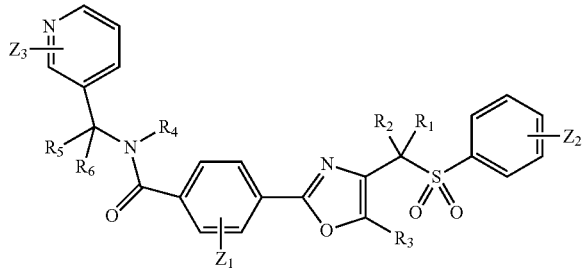

where $R_1$, $R_2$, $R_5$, $R_6$ are independently H, alkyl, alkynyl, cycloalkyl, alkylcycloalkyl, aryl or alkylaryl;

$R_1$ to $R_2$ and $R_5$ to $R_6$ can be joined to form a 3 to 5 member cycloalkyl rings;

$R_3$, $R_4$ are independently H, alkyl, cycloalkyl, alkylcycloalkyl, aryl or alkylaryl;

$Z_1$ are 1 to 4 substituents comprising H, alkyl, cyclopropyl, alkynyl, halogens, hydroxyl, alkoxides, alkylsulfones, alkyl sulfides, cyano, nitro, trifluoromethyl, mono alkyl substituted carboxyamide, alkyl carboxyl ester, amino, monoalkyl amino, aminosulfonyl, sulfonylamino, dialkyl amino or a 5 or 6 membered appended ring comprising carbon or carbon and one or two oxygen or nitrogen atoms;

$Z_2$ are 1 to 5 substituents comprising H, alkyl, cyclopropyl, alkynyl, halogens, hydroxyl, alkoxides, alkylsulfones, alkyl sulfides, cyano, nitro, trifluoromethyl, mono alkyl substituted carboxyamide, alkyl carboxyl ester, amino, monoalkyl amino, aminosulfonyl, sulfonylamino, dialkyl amino or a 5 or 6 membered appended ring comprising carbon or carbon and one or two oxygen or nitrogen atoms; and $Z_3$ are 1 to 4 substituents comprising H, alkyl, cyclopropyl, alkynyl, halogens, hydroxyl, alkoxides, alkylsulfones, alkyl sulfides, cyano, nitro, trifluoromethyl, mono alkyl substituted carboxyamide, alkyl carboxyl ester, amino, monoalkyl amino, aminosulfonyl, sulfonylamino, dialkyl amino or a 5 or 6 membered appended ring comprising carbon or carbon and one or two oxygen or nitrogen atoms.

In some such embodiments, $R_1$, $R_2$, $R_5$, $R_6$ are independently H, alkyl, cycloalkyl;

$R_3$, $R_4$ are independently H, alkyl;

$Z_1$ are 1 to 4 substituents comprising H, alkyl, halogens, hydroxyl, alkoxides, alkylsulfones, alkyl sulfides, cyano, nitro, trifluoromethyl, mono alkyl substituted carboxyamide, alkyl carboxyl ester, amino, monoalkyl amino, aminosulfonyl, sulfonylamino, dialkyl amino;

$Z_2$ are 1 to 5 substituents comprising H, alkyl, halogens, hydroxyl, alkoxides, alkylsulfones, alkyl sulfides, cyano, nitro, trifluoromethyl, mono alkyl substituted carboxyamide, alkyl carboxyl ester, amino, monoalkyl amino, aminosulfonyl, sulfonylamino, dialkyl amino; and $Z_3$ are 1 to 4 substituents comprising H, alkyl, cyclopropyl, alkynyl, halogens, hydroxyl, alkoxides, alkylsulfones, alkyl sulfides, cyano, nitro, trifluoromethyl, mono alkyl substituted carboxyamide, alkyl carboxyl ester, amino, monoalkyl amino, aminosulfonyl, sulfonylamino, dialkyl amino.

In some such embodiments, $R_1$, $R_2$, $R_5$, $R_6$ are H;

$R_3$, $R_4$ are independently H, alkyl;

$Z_1$ comprises H;

$Z_2$ are 1 to 4 substituents comprising H, alkyl, halogens, hydroxyl, alkoxides, alkylsulfones, alkyl sulfides, cyano, nitro, trifluoromethyl, mono alkyl substituted carboxyamide, alkyl carboxyl ester, amino, monoalkyl amino, aminosulfonyl, sulfonylamino, dialkyl amino; and $Z_3$ are 1 to 4 substituents comprising H, alkyl, cyclopropyl, alkynyl, halogens, hydroxyl, alkoxides, alkylsulfones, alkyl sulfides, cyano, nitro, trifluoromethyl, mono alkyl substituted carboxyamide, alkyl carboxyl ester, amino, monoalkyl amino, aminosulfonyl, sulfonylamino, dialkyl amino.

In particular, $R_3$, $R_4$, $Z_2$ and $Z_3$ can be selected from the following table:

| $R_3$ | $R_4$ | $Z_2$ | $Z_3$ |
|---|---|---|---|
| H | H | 4-$CH_3$ | H |
| $CH_3$ | H | H | H |
| $CH_3$ | $CH_3$ | 4-$CH_3$ | H |
| $CH_3$ | H | 3-$CH_3$ | H |
| $CH_3$ | H | 2-$CH_3$ | H |
| $CH_3$ | H | 4-Cl | H |
| $CH_3$ | H | 3-Cl | H |
| $CH_3$ | H | 2-Cl | H |
| $CH_3$ | H | 4-F | H |
| $CH_3$ | H | 3-F | H |
| $CH_3$ | H | 4-CN | H |
| $CH_3$ | H | 3-CN | H |
| $CH_3$ | H | 3-$CF_3$ | H |
| $CH_3$ | H | 4-$CF_3$ | H |

-continued

| $R_3$ | $R_4$ | $Z_2$ | $Z_3$ |
|---|---|---|---|
| $CH_3$ | H | 4-$OCH_3$ | H |
| $CH_3$ | H | 3-$OCH_3$ | H |
| $CH_3$ | H | 3-$NH_2$ | H |
| $CH_3$ | H | 4-$NH_2$ | H |
| $CH_3$ | H | 4-$CH_3$ | 2-CN |
| $CH_3$ | H | 4-$CH_3$ | 2-F |
| $CH_3$ | H | 4-$CH_3$ | 2-F |
| $CH_3$ | H | 4-$CH_3$ | 2-$NO_2$ |
| $CH_2CH_3$ | H | 4-$CH_3$ | H |
| $CH_3$ | H | 4-$CH_2CH_3$ | H |
| $CH_3$ | H | 4-$CH_3$ | 2-$SO_2CH_3$ |
| $CF_3$ | H | 4-$CH_3$ | H |
| $CH_3$ | H | 4-$CH_3$ | 2-$CF_3$ |
| $CH_3$ | H | 4-$CO_2CH_3$ | H |
| $CH_3$ | H | 4-$CONHCH_3$ | H |
| $CH_3$ | H | 4-$CH_3$ | 2-$CONHCH_3$ |
| $CH_3$ | H | 4-$CH_3$ | 2-$CO_2CH_3$ |

In other embodiments, the compound or a salt thereof of the invention has the structure:

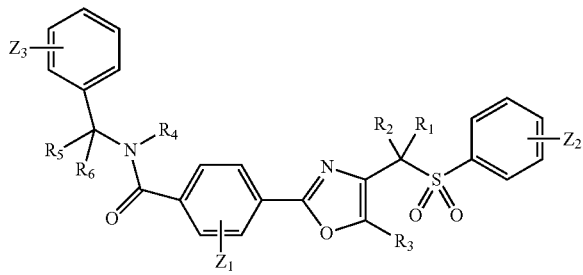

where $R_1$, $R_2$, $R_5$, $R_6$ are independently H, alkyl, alkynyl, cycloalkyl, alkylcycloalkyl, aryl or alkylaryl;

$R_1$ to $R_2$ and $R_5$ to $R_6$ can be joined to form a 3 to 5 member cycloalkyl rings;

$R_3$, $R_4$ are independently H, alkyl, cycloalkyl, alkylcycloalkyl, aryl or alkylaryl;

$Z_1$ are 1 to 4 substituents comprising H, alkyl, cyclopropyl, alkynyl, halogens, hydroxyl, alkoxides, alkylsulfones, alkyl sulfides, cyano, nitro, trifluoromethyl, mono alkyl substituted carboxyamide, alkyl carboxyl ester, amino, monoalkyl amino, aminosulfonyl, sulfonylamino, dialkyl amino or a 5 or 6 membered appended ring comprising carbon or carbon and one or two oxygen or nitrogen atoms;

$Z_2$ are 1 to 5 substituents comprising H, alkyl, cyclopropyl, alkynyl, halogens, hydroxyl, alkoxides, alkylsulfones, alkyl sulfides, cyano, nitro, trifluoromethyl, mono alkyl substituted carboxyamide, alkyl carboxyl ester, amino, monoalkyl amino, aminosulfonyl, sulfonylamino, dialkyl amino or a 5 or 6 membered appended ring comprising carbon or carbon and one or two oxygen or nitrogen atoms; and $Z_3$ are 1 to 5 substituents comprising H, alkyl, cyclopropyl, alkynyl, halogens, hydroxyl, alkoxides, alkylsulfones, alkyl sulfides, cyano, nitro, trifluoromethyl, mono alkyl substituted carboxyamide, alkyl carboxyl ester, amino, monoalkyl amino, aminosulfonyl, sulfonylamino, dialkyl amino or a 5 or 6 membered appended ring comprising carbon or carbon and one or two oxygen or nitrogen atoms.

In some such embodiments, $R_1$, $R_2$, $R_5$, $R_6$ are independently H, alkyl, cycloalkyl;

$R_3$, $R_4$ are independently H, alkyl;

$Z_1$ are 1 to 4 substituents comprising H, alkyl, halogens, hydroxyl, alkoxides, alkylsulfones, alkyl sulfides, cyano, nitro, trifluoromethyl, mono alkyl substituted carboxyamide, alkyl carboxyl ester, amino, monoalkyl amino, aminosulfonyl, sulfonylamino, dialkyl amino;

$Z_2$ are 1 to 5 substituents comprising H, alkyl, halogens, hydroxyl, alkoxides, alkylsulfones, alkyl sulfides, cyano, nitro, trifluoromethyl, mono alkyl substituted carboxyamide, alkyl carboxyl ester, amino, monoalkyl amino, aminosulfonyl, sulfonylamino, dialkyl amino; and $Z_3$ are 1 to 5 substituents comprising H, alkyl, cyclopropyl, alkynyl, halogens, hydroxyl, alkoxides, alkylsulfones, alkyl sulfides, cyano, nitro, trifluoromethyl, mono alkyl substituted carboxyamide, alkyl carboxyl ester, amino, monoalkyl amino, aminosulfonyl, sulfonylamino, dialkyl amino.

In some such embodiments, $R_1$, $R_2$, $R_5$, $R_6$ are H;

$R_3$, $R_4$ are independently H, alkyl;

$Z_1$ comprises H;

$Z_2$ are 1 to 4 substituents comprising H, alkyl, halogens, hydroxyl, alkoxides, alkylsulfones, alkyl sulfides, cyano, nitro, trifluoromethyl, mono alkyl substituted carboxyamide, alkyl carboxyl ester, amino, monoalkyl amino, aminosulfonyl, sulfonylamino, dialkyl amino; and $Z_3$ are 1 to 5 substituents comprising H, alkyl, cyclopropyl, alkynyl, halogens, hydroxyl, alkoxides, alkylsulfones, alkyl sulfides, cyano, nitro, trifluoromethyl, mono alkyl substituted carboxyamide, alkyl carboxyl ester, amino, monoalkyl amino, aminosulfonyl, sulfonylamino, dialkyl amino.

In particular, $R_3$, $R_4$, $Z_2$ and $Z_3$ can be selected from the following table:

| $R_3$ | $R_4$ | $Z_2$ | $Z_3$ |
|---|---|---|---|
| H | H | 4-$CH_3$ | H |
| $CH_3$ | H | H | H |
| $CH_3$ | $CH_3$ | 4-$CH_3$ | H |
| $CH_3$ | H | 3-$CH_3$ | H |
| $CH_3$ | H | 2-$CH_3$ | H |
| $CH_3$ | H | 4-Cl | H |
| $CH_3$ | H | 3-Cl | H |
| $CH_3$ | H | 2-Cl | H |
| $CH_3$ | H | 4-F | H |
| $CH_3$ | H | 3-F | H |
| $CH_3$ | H | 4-CN | H |
| $CH_3$ | H | 3-CN | H |
| $CH_3$ | H | 3-$CF_3$ | H |
| $CH_3$ | H | 4-$CF_3$ | H |
| $CH_3$ | H | 4-$OCH_3$ | H |
| $CH_3$ | H | 3-$OCH_3$ | H |
| $CH_3$ | H | 3-$NH_2$ | H |
| $CH_3$ | H | 4-$NH_2$ | H |
| $CH_3$ | H | 4-$CH_3$ | 3-CN |
| $CH_3$ | H | 4-$CH_3$ | 4-F, 3-CN |
| $CH_3$ | H | 4-$CH_3$ | 2-F |
| $CH_3$ | H | 4-$CH_3$ | 3-F |
| $CH_3$ | H | 4-$CH_3$ | 3-$NO_2$ |
| $CH_2CH_3$ | H | 4-$CH_3$ | H |
| $CH_3$ | H | 4-$CH_2CH_3$ | H |
| $CH_3$ | H | 4-$CH_3$ | 3-$SO_2CH_3$ |
| $CF_3$ | H | 4-$CH_3$ | H |
| $CH_3$ | H | 4-$CH_3$ | 3-$CF_3$ |
| $CH_3$ | H | 4-$CH_3$ | 2-F, 3-F |
| $CH_3$ | H | 4-$CH_3$ | 3-F, 4-F |
| $CH_3$ | H | 4-$CO_2CH_3$ | 3-F |
| $CH_3$ | H | 4-$CH_3$ | 3-F, 4-$CO_2CH_3$ |
| $CH_3$ | H | 4-$CH_3$ | 3-$CONHCH_3$ |
| $CH_3$ | H | 4-$CH_3$ | 3-$CO_2CH_3$ |
| $CH_3$ | H | 4-$CO_2CH_3$ | 3-F |
| $CH_3$ | H | 4-$CONHCH_3$ | 3-F |

Dosage Forms of Compounds of the Present Disclosure

In pharmaceutical dosage forms, the compounds disclosed herein may be administered in the form of their pharmaceutically acceptable salts, or they may also be used alone or in appropriate association, as well as in combination, with other pharmaceutically active compounds. The following methods and excipients are merely exemplary and are in no way limiting.

The agent can be administered to a host using any available conventional methods and routes suitable for delivery of conventional drugs, including systemic or localized routes. In general, routes of administration contemplated include but are not necessarily limited to, enteral, parenteral, or inhalational routes, such as intrapulmonary or intranasal delivery.

Conventional and pharmaceutically acceptable routes of administration include intranasal, intrapulmonary, intramuscular, intratracheal, subcutaneous, intradermal, topical application, intravenous, rectal, nasal, oral and other parenteral routes of administration. Routes of administration may be combined, if desired, or adjusted depending upon the agent and/or the desired effect. The composition can be administered in a single dose or in multiple doses.

For oral preparations, the subject compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. If oral administration is desired, the subject compounds may optionally be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Parenteral routes of administration other than inhalation administration include, but are not necessarily limited to, topical, transdermal, subcutaneous, intramuscular, intraorbital, intracapsular, intraspinal, intrasternal, and intravenous routes. Parenteral administration can be carried to effect systemic or local delivery of the agent. Where systemic delivery is desired, administration typically involves invasive or systemically absorbed topical or mucosal administration of pharmaceutical preparations. Where local delivery is desired, administration typically involves administering the composition to a desired target tissue, such a liver, heart, spine, etc. For local delivery, the administration may be by injection or by placement of the composition in the desired tissue or organ by surgery, for example.

Methods of administration of the agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

The subject compounds of the invention can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agent can also be delivered to the subject by enteral administration. Enteral routes of administration include, but are not necessarily limited to, oral and rectal (e.g., using a suppository) delivery.

Furthermore, the subject compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Dosages of the Compounds of the Present Disclosure

Depending on the subject and condition being treated and on the administration route, the subject compounds may be administered in dosages of, for example, 0.1 μg to 100 mg/kg body weight per day. The range is broad, since in general the efficacy of a therapeutic effect for different mammals varies widely with doses typically being 20, 30 or even 40 times smaller (per unit body weight) in man than in the rat. Similarly the mode of administration can have a large effect on dosage. Thus, for example, oral dosages may be about ten times the injection dose. Higher doses may be used for localized routes of delivery.

A typical dosage may be a solution suitable for intravenous administration; a tablet taken from one to six times daily, or one time-release capsule or tablet taken once a day and containing a proportionally higher content of active ingredient, etc. The time-release effect may be obtained by capsule materials that dissolve at different pH values, by capsules that release slowly by osmotic pressure, or by any other known means of controlled release.

Those of skill in the art will readily appreciate that dose levels can vary as a function of the specific compound, the severity of the symptoms and the susceptibility of the subject to side effects. Preferred dosages for a given compound are readily determinable by those of skill in the art by a variety of means.

Although the dosage used will vary depending on the clinical goals to be achieved, a suitable dosage range is one which provides up to about 1 μg to about 1,000 μg or about 100,000 μg of subject composition to reduce a symptom in a subject animal.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the invention. Similarly, unit dosage forms for injection or intravenous administration may comprise the compound (s) in a composition as a solution in sterile water, normal saline or another pharmaceutically acceptable carrier.

Combination Therapy Using the Compounds of the Invention

For use in the subject methods, the subject compounds may be formulated with or otherwise administered in combination with other pharmaceutically active agents, including other chemotherapeutic agents.

The compounds described above may also be administered in combination with other therapies for cancer treatment, including without limitation MLL translocation associated leukemia. The compounds described above may be administered before, after, or during another therapy for cancer.

These chemotherapeutic agents may be categorized by their mechanism of action into, for example, the following groups: anti-metaboliteslanti-cancer agents, such as pyrimidine analogs (e.g., 5-fluorouracil, floxuridine, capecitabine, gemcitabine and cytarabine) and purine analogs, folate antagonists and related inhibitors (e.g., mercaptopurine, thioguanine, pentostatin and 2-chlorodeoxyadenosine (cladribine)); antiproliferative/antimitotic agents including natural products such as vinca alkaloids (e.g., vinblastine, vincristine, and vinorelbine), microtubule disruptors such as taxane (paclitaxel, docetaxel), vincristin, vinblastin, nocodazole, epothilones and navelbine, epipidophyllotoxins (teniposide), DNA damaging agents (e.g., actinomycin, amsacrine, anthracyclines, bleomycin, busulfan, camptothecin, carboplatin, chlorambucil, cisplatin, cyclophosphamide, cytoxan, dactinomycin, daunorubicin, docetaxel, doxorubicin, epirubicin, hexamethylmelamineoxaliplatin, iphosphamide, melphalan, merchlorethamine, mitomycin, mitoxantrone, nitrosourea, paclitaxel, plicamycin, procarbazine, teniposide, triethylenethiophosphoramide and etoposide (VPI 6)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (e.g., L-asparaginase, which systemically metabolizes L-asparagine and deprives cells which do not have the capacity to synthesize their own asparagine); antiplatelet agents; antiproliferative/antimitotic alkylating agents such as nitrogen mustards (e.g., mechlorethamine, cyclophosphamide and analogs, melphalan, chlorambucil), ethylenimines and methylmelamines (e.g., hexamethylmelamine and thiotepa), alkyl sulfonatesbusulfan, nitrosoureas (e.g., carmustine (BCNU) and analogs, streptozocin), trazenes—dacarbazinine (DTIC); antiproliferative/antimitotic antimetabolites such as folic acid analogs (e.g., methotrexate); platinum coordination complexes (e.g., cisplatin, carboplatin), procarbazine, hydroxyurea, mitotane, aminoglutethimide; hormones, hormone analogs (e.g., estrogen, tamoxifen, goserelin, bicalutamide, nilutamide) and aromatase inhibitors (e.g., letrozole, anastrozole); anticoagulants (e.g., heparin, synthetic heparin salts and other inhibitors of thrombin); fibrinolytic agents (such as tissue plasminogen activator, streptokinase and urokinase), aspirin, COX-2 inhibitors, dipyridamole, ticlopidine, clopidogrel, abciximab; antimigratory agents; antisecretory agents (e.g., breveldin); immunosuppressives (e.g., cyclosporine, tacrolimus (FK-506), sirolimus (rapamycin), azathioprine, mycophenolate mofetil); anti-angiogenic compounds (e.g., TNP-470, genistein) and growth factor inhibitors (e.g., vascular endothelial growth factor (VEGF) inhibitors, fibroblast growth factor (FGF) inhibitors, epidermal growth factor (EGF) inhibitors); angiotensin receptor blocker; nitric oxide donors; anti-sense oligonucleotides; antibodies (e.g., trastuzumab and others listed above); cell cycle inhibitors and differentiation inducers (e.g., tretinoin); mTOR inhibitors, topoisomerase inhibitors (e.g., doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (e.g., cortisone, dexamethasone, hydrocortisone, methylpednisolone, prednisone, and prenisolone); growth factor signal transduction kinase inhibitors; mitochondrial dysfunction inducers and caspase activators; chromatin disruptors.

The compounds described herein for use in combination therapy with the compounds of the present invention may be administered by the same route of administration (e.g. intrapulmonary, oral, enteral, etc.) that the compounds are administered. In the alternative, the compounds for use in combination therapy with the compounds of the present invention may be administered by a different route of administration that the compounds are administered.

Kits

Kits with unit doses of the subject compounds, usually in oral or injectable doses, are provided. In such kits, in addition to the containers containing the unit doses will be an informational package insert describing the use and attendant benefits of the drugs in treating pathological condition of interest. Preferred compounds and unit doses are those described herein above.

Methods of Use

Aspects of the invention include methods of using the subject anti-proliferative compounds, e.g., as described above, to inhibit the growth of cancer cells. In practicing methods of the invention, the cells of interest are contacted with an effective amount of an anti-proliferative compound, e.g., as described above. By effective amount is meant an amount of the anti-proliferative compound that is sufficient to inhibit the growth of the target cell population to a desired level.

In practicing methods of the invention, the cells of interest may be contacted with the effective amount of the anti-proliferative compound in an in vitro or ex vivo culture system, or in vivo. For example, an anti-proliferative compound may be contacted to primary cells grown under standard tissue culture conditions or alternatively to cells that are part of a whole animal (e.g., administered to a subject). As such, the target cell or collection of cells may vary, where the collection of cells may be cultured cells, a whole animal or portion thereof, e.g., tissue, organ, etc. As such, the target cell(s) may be a host animal or portion thereof.

Cells of interest include without limitation leukemia cells that include a genetic abnormality in the MLL gene. Such cells are described, e.g., by Krivtsov and Armstrong ("MLL translocations, histone modifications and leukaemia stem-cell development. *Nature Reviews Cancer* 7, 823-833 (2007)).

In the subject methods, the anti-proliferative compound may be contacted with the target cells using any convenient protocol that results in the desired level of anti-proliferative activity. Thus, the anti-proliferative compound can be incorporated into a variety of pharmaceutical compositions for therapeutic administration, e.g., as described above. For example, the anti-proliferative compound can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments (e.g., skin creams), solutions, suppositories, injections, inhalants and aerosols, such as described above. As such, administration of the anti-proliferative compound can be achieved in various ways, including oral, buccal, rectal, parenteral, intraperitoneal, intradermal, transdermal, intracheal, etc., administration.

The subject methods find use in the treatment of a variety of different conditions in which inhibition of the growth of cancer cells in the host is desired. By treatment is meant that at least an amelioration of the symptoms associated with the condition afflicting the host is achieved, where amelioration is used in a broad sense to refer to at least a reduction in the magnitude of a parameter, e.g. symptom (such as tumor growth or cell population growth), associated with the condition being treated. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

The anti-proliferative compounds, e.g., as described above, find use in a variety of applications. Applications of interest include, but are not limited to: therapeutic applications, research and manufacturing applications, and screening applications.

Therapeutic Applications

Anti-proliferative compounds of the invention find use in a variety of therapeutic applications. Therapeutic applications of interest include, without limitation, those applications in which the growth and spread of leukemia cells is the cause or a compounding factor in disease progression. As such, the subject compounds find use in the treatment of a variety of different conditions in which inhibition of leukemia in the host is desired. Examples of disease conditions/disorders and therapeutic applications which may be treated with compounds of the invention include, but are not limited to: cancer and other proliferative diseases, such as leukemia (e.g., MLL translocation associated leukemia).

The subject treated in the present methods can be a human subject, although it is to be understood that the principles of the invention indicate that the invention is effective with respect to all mammals.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); Room Temperature, RT, rt, and the like.

A cell-based high-throughput phenotypic screen was conducted to identify compounds that selectively inhibit the growth of human cell lines representative of high-risk B-ALL. Cell viability was assessed using a fluorescent indicator dye at 2 days after addition of compounds.

Out of 130,000 compounds screened, 60 were identified as inhibiting proliferation of one or both MLL leukemia cell lines (RS411-MLL-AF4; HB-MLL-ENL) representative of high-risk ALL while not affecting the "control" cells (REH-TEL-AML) representative of low-risk ALL. Compounds that reduced viability of all cell lines, such as the anthracycline idarubicin, were excluded as candidates. The 60 selective candidates were retested on additional ALL cell lines with and without MLL translocations. Eight compounds were found to preferentially inhibit cell lines with MLL translocations.

Example 1

Inhibitors of Human and Murine Cancer Cells and Cell Lines

The compounds have broad specificity and affect human cell lines of multiple lineages. The growth inhibitory properties were analyzed in human cancer cell lines derived from 9 different tissues in the NCI 60-cell line screen. To perform this assay, cells were plated in 96-well plates and incubated overnight. After 24 hours, compounds were added to the wells and plates. Two plates of each cell line were set aside and fixed in TCA to measure the quantity of cells present at the time drug was added (time 0). The remaining plates were incubated for 48 hours. The assay was terminated by addition of TCA, and the cells were quantified by staining the cellular proteins with sulforhadamine B. The growth inhibition ($GI_{50}$) was calculated by dividing the difference between treated cells at the beginning and end of the assay by the difference between untreated cells at the beginning and end of the assay.

All compounds affected multiple cell line types in this assay. Compound 1 showed particularly high activity in colon and prostate cancer cell lines, suggesting the compounds also have therapeutic applications in colon and prostrate cancer. These data are illustrated in FIGS. 1 and 2.

Figure 3:
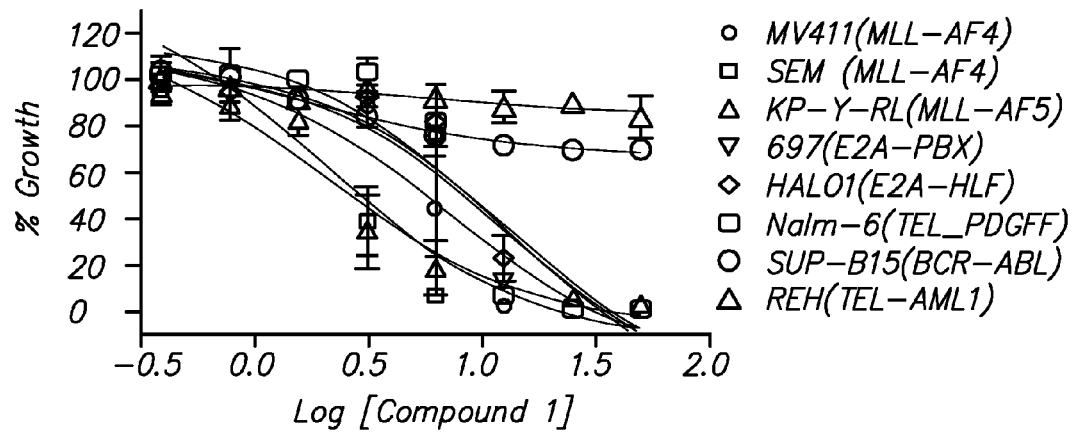
FIG. 3. Inhibition of human B-ALL cell lines treated with compound. Cell lines were treated with increasing concentrations of compound and assessed for viability 3 days post-treatment by cell titer blue assay.

The majority of human leukemia cell lines with MLL translocations (3/4) were inhibited more potently than non-MLL cell lines (FIG. 3); although most non-MLL cells lines (4/6) were still sensitive to the compounds. Compound 1 is the most potent with an $IC_{50}$ (half maximal inhibitory concentration) of 1-10 nM on cell lines with MLL translocations and 10-20 nM on cells lines with other translocations (E2A-PBX, E2A-HLF, TEL-PDGFRB). Compound 1 also has inhibitory effects on primary human patient ALL samples with an $IC_{50}$ of 4-20 nM.

Compound 1 was also tested for its effects on murine leukemia cell lines established from AMLs induced via retroviral transduction of MLL fusion oncogenes (Somervaille, T. C. & Cleary, M. L. Identification and characterization of leukemia stem cells in murine MLL-AF9 acute myeloid leukemia. *Cancer Cell* 10, 257-268, (2006)). AML cell lines induced by MLL-AF10 or MLL-AF9 were highly sensitive to compound 1.

Compound 1 has a similar potency to idarubicin, an anthracycline that is currently used to treat AML and ALL, but has a wider therapeutic window. Idarubicin kills human B-ALL cell lines and normal murine bone marrow progenitors with overlapping potency. However, human B-ALL cells and murine bone marrow progenitor cells have differential sensitivity to compound 1. These analyses suggest that compound 1 has a wider therapeutic window than anthracyclines with potentially less toxicity.

Compound 1 induced death of human and mouse leukemia cell lines by apoptosis (annexin V and propidium iodide staining) within 3 days of a single treatment, indicating a cytotoxic as opposed to cytostatic effect. The kinetics of cell death (initiation at 24 hours, completion at 48 hours) after treatment suggests that the compound 1 exerts cytotoxic effects via DNA or protein binding.

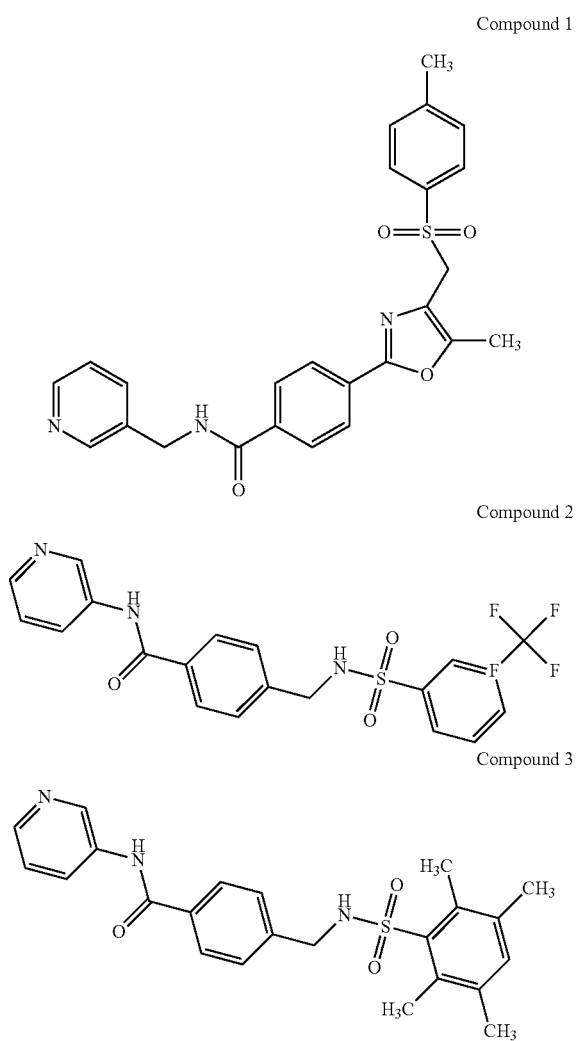

In a mouse model of AML induced by MLL oncogenes, the leukemic colony forming cells (CFCs) represent leukemia stem cells (LSCs) since single colonies induce AML in recipient mice following transplantation (Somervaille, T. C. & et al. Hierarchical maintenance of MLL myeloid leukemia stem cells employs a transcriptional program shared with embryonic rather than adult stem cells. Cell Stem Cell 4, 129-140, (2009)). LSCs have been well defined in this model allowing for specific assessment of their sensitivity to lead compound. Therefore, CFC assays were used as a surrogate method to assess the effects on LSCs. The lead compound inhibited CFC formation by AML cells induced by MLL-AF9 with high potency suggesting activity against LSCs in this model.

Pharmacokinetic Properties of Compound 1

Initial pharmacokinetic studies were conducted in mice to inform design of pre-clinical efficacy studies. Compound 1, which is hydrophobic and sparingly soluble, was formulated in 10% DMSO and 40% captisol, which is amenable to filter sterilization and delivery to mice via intra-peritoneal, intravenous, or subcutaneous routes. Following a single intra-peritoneal or subcutaneous injection (16 mg/kg) compound 1 was quickly absorbed in plasma and its concentration rapidly peaked and decreased over 24 hours. Similar pharmacokinetics were observed in studies delivering 25 mg/kg compound formulated in 5% DMSO and 20% gamma-cyclodextrin via intra-peritoneal, subcutaneous, and oral routes. The half-life was determined to be roughly 1.5 hours, and at 24 hours almost no compound remained in the plasma. These results showed that the compound is absorbed into plasma and rapidly cleared with a short half-life.

Preliminary toxicity studies were performed. Mice were injected (vehicle alone, 8 mg/kg, or 16 mg/kg) daily over a 10 day-period with a 2-day holiday after the first 4 days. All but one animal tolerated dosing and did not show signs of distress or body weight reduction indicating that the MTD or lethal dose was not achieved. Severe cardiotoxicity in one animal and mild cardiotoxicity in another animal, both in the high-dose group suggest that cardiotoxicity may be a limiting toxicity. Mild nephrotoxicity, a known reversible feature of β-cyclodextrins such as captisol, was observed in a minority of animals, including animals only treated with vehicle (Stella, V. & Quanren, H., Cyclodextrins. Toxicologic Pathology 36, 30-42 (2008)).

An additional toxicity study was performed by injecting mice subcutaneously twice a day with 20 mg/kg compound formulated in 5% DMSO/20% gamma-cyclodextrin or 22.5 mg/kg compound formulated in 10% DMSO/40% captisol. for 10 consecutive days. Animals were also dosed with gamma-cyclodextrin or captisol vehicle alone. No toxic side effects were observed in tissue morphology in histological analysis or serological tests of liver and kidney function. No nephrotoxicity was observed in animals treated with the gamma-cyclodextrin formulation.

Example 2

Optimization of Structure Activity Relationships of Compounds

The chemical space surrounding lead compounds was explored through high-throughput screening of analogs to establish structure-activity relationships. The analogs, which are structurally similar to the active compounds, were acquired and prepared for a high-throughput screen. The compounds were selected to provide appropriate variability to identify the critical functional groups of the parent compound. The compounds were tested on ten human leukemia cell lines (5 with MLL rearrangements, 5 without).

Based on SAR results, active compounds are chemically modified by a chemical cross-linker onto dispensable side chains to allow for immobilization of the modified compounds on beads to allow identification of compound-small molecule interactions (Rix, U. & Superti-Furga, G. Target profiling of small molecules by chemical proteomics. Nat Chem Biol 5, 616-624, (2009)). Non-specific DNA binding has been ruled out as a mechanism of action via Biacore studies. After exposure to cell lysates, pull-down assays are performed to isolate protein-compound complexes (Ong, S. E. et al. Identifying the proteins to which small-molecule probes and drugs bind in cells. Proc Natl Acad Sci USA 106, 4617-4622, (2009)). Mass spectrometry is used to identify proteins bound to the active compounds. To distinguish proteins that non-specifically bind the compound or beads, parallel analyses are performed employing an inactive compound analog that is similarly modified with cross-linker to serve as a reference.

As an alternative approach, biological modes of action are interrogated using gene expression profiling of treated cells in combination with bioinformatic analysis resulting datasets for connectivity with molecular signatures induced by known chemical compounds and drugs (Lamb, J., et al. The Connectivity Map: using gene-expression signatures to connect small molecules, genes, and disease. *Science* 5795, 1929-35 (2006)). Candidate targets/pathways identified by biochemical or bioinformatic approaches are validated through genetic studies employing shRNA knock-down and/or genetically deficient mouse cells using in vitro and in vivo transformation models.

Example 3

Efficacy of Compounds in Mouse Models of Leukemia

An amount of compound 1 was synthesized for use in pre-clinical efficacy studies. The formulation was selected to minimize side effects from the carrier. For example, formulations using a high concentration of captisol cause mild nephrotoxicity.

The in vivo efficacy of compound 1 was assessed in a xenograft model of human B-ALL. In this model, immunocompromised (NSG) mice transplanted with the MV411 (MLL-AF4) human leukemia cell line invariably succumb to disease within 35-37 days. The MV411 cell line was genetically modified to constitutively express firefly luciferase, which permits bioluminescent imaging for non-invasive monitoring of tumor progression during efficacy studies.

Preliminary studies established that the MV411-lucifease cell line is highly sensitive to compound 1 with an $IC_{50}$ of 10 nM and an $IC_{100}$ of 25 nM (±20 nM). Pre-incubation of compound with FBS prior to cell treatment in vitro showed no effect on potency suggesting that protein binding in plasma is not a factor for compound activity in vivo. The target plasma concentration of 100 nM is readily achievable as established in preliminary pharmacokinetic studies.

Immunocompromised (NSG) mice were injected via tail vein with $5\times10^6$ MV411-lucif erase cells. Treatment with compound was initiated at day 13 when bioluminescence was detectable. Animals were treated subcutaneously for 20 days consecutively. Leukemia progression was monitored via bioluminescent imaging every 3 days. A response indicates that the compound eradicated tumor or prevented progression. During the study blood was collected for determination of $C_{max}$ and $C_{min}$.

Figure 4:
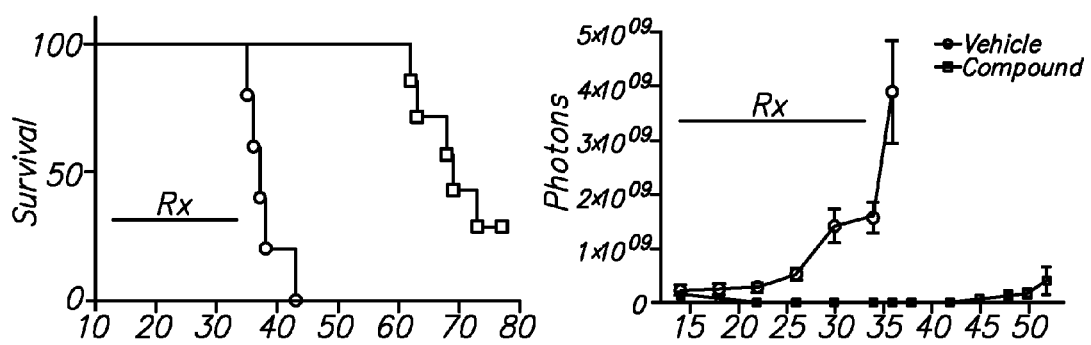
FIG. 4. Efficacy of lead compound in preclinical model of acute leukemia. Left panel displays survival of mice treated with vehicle or lead compound initiating at day 13 following injection of human leukemia cell line. Right panel shows mean bioluminescence signal intensities for mice in the two cohorts at the indicated days.

Compound treated mice showed a substantial prolongation of survival compared to vehicle treated control mice, which succumb to leukemia as expected (FIG. 4). Notably, there was a significant and persistent reduction of bioluminescence signal throughout the treatment period indicating a substantial cytotoxic effect in vivo (FIG. 4). These results demonstrated that the lead compound has significant efficacy in a pre-clinical xenograft model of human acute leukemia.

Efficacy studies are refined and extended as necessary and appropriate. Formulation and route of administration is adjusted to achieve the most favorable efficacy and toxicity profiles. Depending on results, the model is extended to primary patient samples.

Example 4

A general method to prepare certain compounds of the invention is as follows presented below:

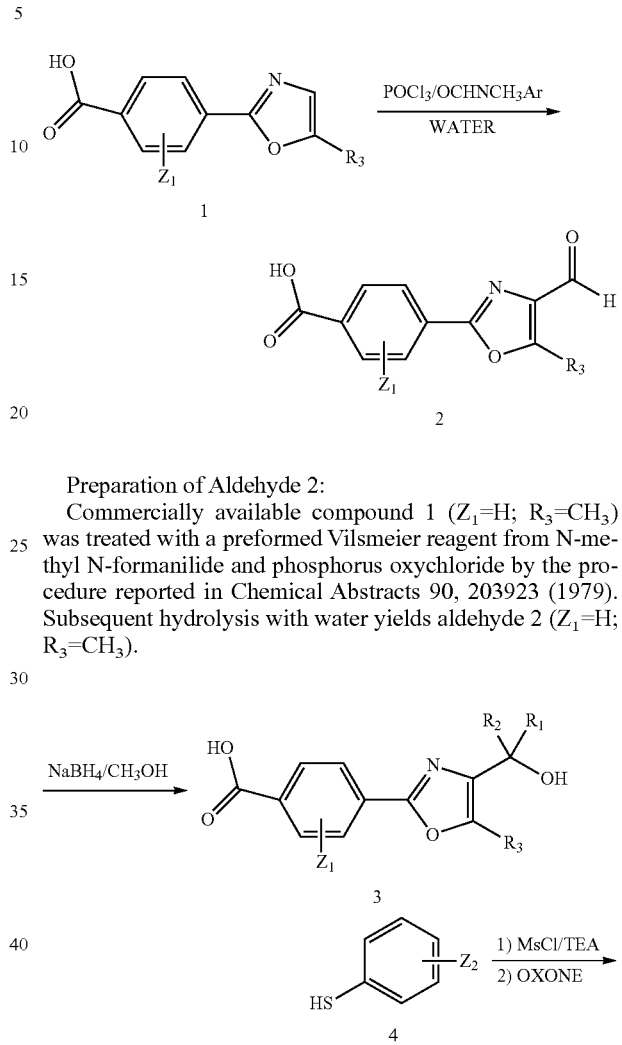

Preparation of Aldehyde 2:

Commercially available compound 1 ($Z_1$=H; $R_3$=$CH_3$) was treated with a preformed Vilsmeier reagent from N-methyl N-formanilide and phosphorus oxychloride by the procedure reported in Chemical Abstracts 90, 203923 (1979). Subsequent hydrolysis with water yields aldehyde 2 ($Z_1$=H; $R_3$=$CH_3$).

Preparation of Compound 5:

Aldehyde 2 is reduced with sodium borohydride in a methanol solution to yield alcohol 3 ($Z_1$=H; $R_1$/$R_2$=H; $R_3$=$CH_3$). The methanol is evaporated away and the residue is acidified with 1N aqueous HCl. Compound 3 is extracted from the aqueous suspension with methylene chloride. The solvent is removed and the product crystallized for methylene chloride and ether. Compound 3 is dissolved in methylene chloride and 5 equivalents triethyl amine (TEA) with a trace of 4-dimethylaminopyridine (DMAP) then the stirred solution is cooled to 0° C. Mesyl chloride (1.2 eq.) is added slowly as temperature in maintained a 0° C. After stirring 1 hour, 1.1 equivalents of thiol 4 ($Z_2$=4-$CH_3$) dissolved in methylene chloride is slowly added. This reaction mixture is allowed to warm to room temperature and stirring is continued overnight. The mixture is diluted with 1N aqueous HCl and the methylene chloride layer separated. The organic layer containing the sulfide product is washed three times with water and dried over anhydrous magnesium sulfate. The drying agent is removed by filtration and the product containing solution concentrated to dryness. The oily foul smelling residue was re-dissolved in tetrahydrofuran (THF) and 2.5 equivalents of OXONE dissolved in the minimum amount of water is added to the THF solution of sulfide with rapid stirring of the reaction. The mixture is stirred for 3 hours at room temperature then diluted with methylene chloride and 1N HCl. The mixture is vigorously shaken then the layers separated. The organic layer is washed three times with water and the organic layer dried over anhydrous magnesium sulfate. After removing the drying agent, the product sulfone, 5 ($Z_1$=H; $Z_2$=4-$CH_3$; $R_1/R_2$=H; $R_3$=$CH_3$), is recrystallized from a mixture methylene chloride and diethyl ether.

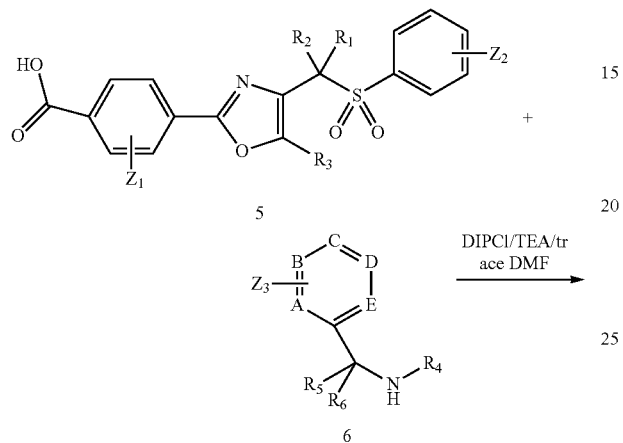

Preparation of Target Compound 7:

Sulfone, 5 ($Z_1$=H; $Z_2$=4-$CH_3$; $R_1/R_2$=H; $R_3$=$CH_3$), is dissolved in methylene chloride, 1.1 equivalents of TEA and a trace of dimethyl formamide (DMF) and DMAP. The stirred solution is cooled to 0° C. and then 1.1 equivalent of diisopropylcarbodiimide (DIPCI) in methylene chloride as added. The reaction is stirred for one hour. To the reaction mixture is slowly added a solution of amine 6 ($Z_3$=3-F; $R_5/R_6$=H; $R_4$=H, A-E=C) dissolved in methylene chloride. The mixture is allowed to warm to room temperature and stirred overnight. The solvent is removed and the residue chromatographed on silica gel using variable gradient hexane/ethyl acetate as the eluting solvents. The product, 7 ($Z_1$=H; $R_1/R_2$=H; $Z_2$=4-$CH_3$; $R_3$=$CH_3$; $Z_3$=3-F; $R_5/R_6$=H; $R_4$=H; A-EC) is then isolated and recrystallized from methylene chloride and diethyl ether.

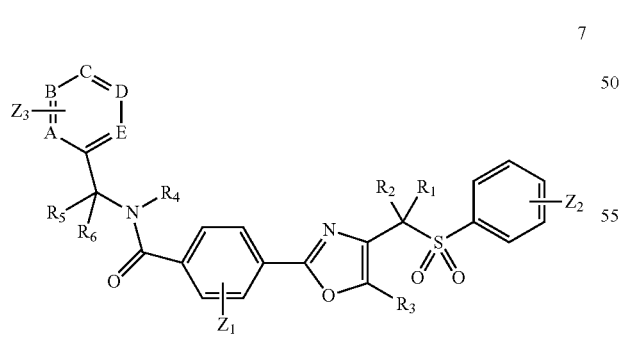

Alternative preparation of compound 10, a general precursor to alcohols of type 3: Compound 10 is prepared via the Robinson-Gabriel oxazole synthesis. Amino acetoacetate 9 is treated with 1 equivalent of chloride 8 in water containing excess sodium bicarbonate. This adduct is then cyclized to the oxazole 10 using a dehydrating agent like polyphosphoric acid (PPA) or thionyl chloride. Reduction of the methyl ester with lithium borohydride yields alcohol 3 ($Z_1$=H; $R_1/R_2$=H; $R_3$=$CH_3$). [Ref. Science of Synthesis, 11, 451 (2001); D. Palmer, Heterocyclic Compounds, 60, 111-117 Wiley-Interscience (2002)]

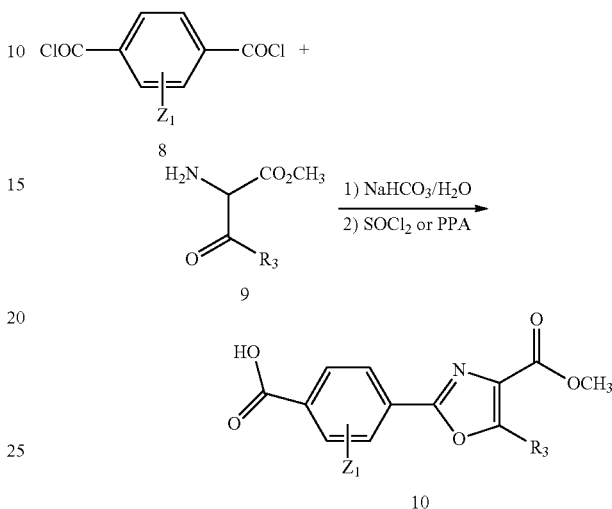

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of inhibiting the growth of leukemia cells, wherein the leukemia cells comprise a genetic abnormality in the MLL gene, the method comprising contacting the leukemia cells with an effective dose of a compound of the structure:

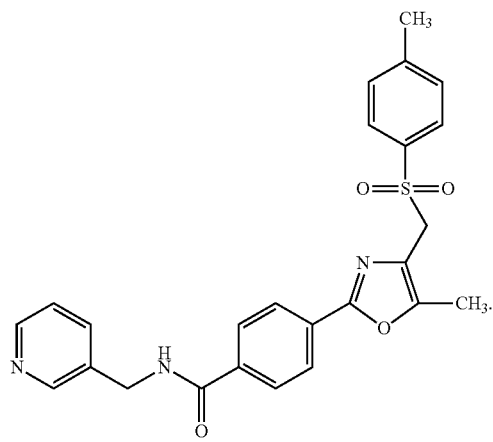 [SMILES: Cc1ccc(S(=O)(=O)Cc2nc(-c3ccc(C(=O)NCc4cccnc4)cc3)oc2C)cc1]

* * * * *

UNITED STATES PATENT AND TRADEMARK OFFICE
CERTIFICATE OF CORRECTION

| | | |
|---|---|---|
| PATENT NO. | : 9,150,559 B2 | Page 1 of 1 |
| APPLICATION NO. | : 14/117571 | |
| DATED | : October 6, 2015 | |
| INVENTOR(S) | : Michael L. Cleary | |

It is certified that error appears in the above-identified patent and that said Letters Patent is hereby corrected as shown below:

IN THE SPECIFICATION

Column 1, Line 6-8 please replace paragraph, as shown below:

GOVERNMENT RIGHTS

This invention was made with Government support under contract CA116606 awarded by the National Institutes of Health. The Government has certain rights in the invention.

Signed and Sealed this
Twenty-second Day of March, 2016

Michelle K. Lee
*Director of the United States Patent and Trademark Office*